US008697380B2

(12) United States Patent
Doumazane et al.

(10) Patent No.: US 8,697,380 B2
(45) Date of Patent: Apr. 15, 2014

(54) METHOD FOR DETECTING COMPOUNDS MODULATING DIMERS OF VFT DOMAIN MEMBRANE PROTEINS

(75) Inventors: Etienne Doumazane, Montpellier (FR); Jurriaan Zwier, Rochefort du Gard (FR); Eric Trinquet, Pont Saint Esprit (FR); Jean-Phillippe Pin, Montpellier (FR)

(73) Assignees: CIS Bio International, Gif sur Yvette Cedex (FR); Centre National de la Recherche Scientifique, Paris (FR)

( * ) Notice: Subject to any disclaimer, the term of this patent is extended or adjusted under 35 U.S.C. 154(b) by 8 days.

(21) Appl. No.: 13/266,222

(22) PCT Filed: Apr. 29, 2010

(86) PCT No.: PCT/FR2010/050814
§ 371 (c)(1),
(2), (4) Date: Dec. 28, 2011

(87) PCT Pub. No.: WO2010/125314
PCT Pub. Date: Nov. 4, 2010

(65) Prior Publication Data
US 2012/0115176 A1 May 10, 2012

(30) Foreign Application Priority Data
Apr. 30, 2009 (FR) ...................................... 09 52908

(51) Int. Cl.
C12Q 1/02 (2006.01)
C12Q 1/34 (2006.01)
C12Q 1/48 (2006.01)

(52) U.S. Cl.
USPC .................................. 435/15; 435/18; 435/29

(58) Field of Classification Search
USPC ............................................. 435/15, 18, 29
See application file for complete search history.

(56) References Cited

U.S. PATENT DOCUMENTS

| | | | |
|---|---|---|---|
| 4,637,988 A | 1/1987 | Hinshaw et al. |
| 4,670,572 A | 6/1987 | Hinshaw et al. |
| 4,761,481 A | 8/1988 | Hale et al. |
| 4,794,191 A | 12/1988 | Hinshaw et al. |
| 4,801,722 A | 1/1989 | Hinshaw et al. |
| 4,837,169 A | 6/1989 | Toner |
| 4,859,777 A | 8/1989 | Toner |
| 5,032,677 A | 7/1991 | Hale et al. |
| 5,055,578 A | 10/1991 | Hale et al. |
| 5,106,957 A | 4/1992 | Hale et al. |
| 5,116,989 A | 5/1992 | Hale et al. |
| 5,202,423 A | 4/1993 | Kankare et al. |
| 5,316,909 A | 5/1994 | Xu |
| 5,324,825 A | 6/1994 | Kankare et al. |
| 5,622,821 A | 4/1997 | Selvin et al. |
| 6,800,651 B2 | 10/2004 | Coleman et al. |
| 6,824,990 B1 | 11/2004 | Blumer |

FOREIGN PATENT DOCUMENTS

| | | |
|---|---|---|
| EP | 0403593 | 12/1990 |
| EP | 1 865 316 | 12/2007 |
| WO | WO90/00550 | 1/1990 |
| WO | WO2004/072232 | 8/2004 |
| WO | WO 2005/033709 | 4/2005 |
| WO | WO 2007/026099 | 3/2007 |
| WO | WO2008/063721 | 5/2008 |
| WO | WO2009/010580 | 1/2009 |

OTHER PUBLICATIONS

Kunishima et al.: "Structural basis of glutamate recognition by a dimeric metabotropic glutamate receptor"; Nature, vol. 407 (6807); Oct. 2000, pp. 971-977.
Tsuchiya et al.: "Structural views of the ligand-binding cores of a metabotropic glutamate receptor complexed with an antagonist and both glutamate and $Gd^{3+}$"; Proc Natl Acad Sci (PNAS) USA, vol. 99, No. 5, Mar. 2002, pp. 2660-2665.
Maurel et al.: "Cell-surface protein-protein interaction analysis with time-resolved FRET and snap-tag technologies: application to GPCR oligomerization"; Nature Methods, Advance Online Publication, May 2008; DOI:10.1038/NMETH.1213, http://www.nature.com/naturemethods.
Maurel et al.: "Cell-surface protein-protein interaction analysis with time-resolved FRET and snap-tag technologies: application to GPCR oligomerization"; Supplementary figures and text, May 2008, Nature Methods.
Maurel et al.: hal-00318856, version 1-5, Sep. 2008; Supplementary method; Ref.: Selvin, P.R. & Hearst, J.R. (1994) Proc Natl Acad Sci USA 91, pp. 10024-10028.
Ferraguti et al.: "Metabotropic glutamate receptors"; Cell Tissue Res. (2006) pp. 326:483-504, DO1 0.1007/s00441-006-0266-5.
Malitschek et al.: "The N-Terminal Domain of γ-Aminobutyric $Acid_B$ Receptors Is Sufficient to Specify Agonist and Antagonist Binding"; Molecular Pharmacology, Accelerated Communication, 56: pp. 448-454 (1999).

(Continued)

Primary Examiner — Chih-Min Kam
(74) Attorney, Agent, or Firm — Hamre, Schumann, Mueller & Larson, P.C.

(57) ABSTRACT

The invention relates to a method for selecting compounds having a modulating effect on the activation state of a dimer of VFT-domain proteins expressed in cell membranes present in a measuring medium, said dimer consisting of a first protein and of a second protein, said proteins being identical or different, wherein this method comprises the following steps:
(a) labeling the first and second proteins in the N-terminal portion of their VFT domains with the members of a pair of FRET partners, the Förster radius ($R_0$) of said pair being between 20 and 55 Å;
(b) measuring the FRET signal in the absence and in the presence of the test compound within a predetermined time window;
(c) selecting the test compound as a modulating compound if a difference in FRET signal in the absence and in the presence of test compound is measured in step (b).
The invention can be used in the search for new medicaments and new taste modulators.

15 Claims, 8 Drawing Sheets

(56) References Cited

OTHER PUBLICATIONS

Liu et al.: "Molecular Determinants Involved in the Allosteric Control of Agonist Affinity in the Gabab Receptor by the $GABA_{B2}$ Subunit"; XP-002556320, The Journal of Biological Chemistry; vol. 279, No. 16, Issue of Apr. 16, pp. 15824-15830 (2004).

Poole et al.: "Synthesis and characterization of highly emissive and kinetically stable lanthanide complexes suitable for usage 'in cellulo'"; The Royal Society of Chemistry 2005; Org. Biomol. Chem., 2005, 3, pp. 1013-1024, www.rsc.org/obc.

Griffin et al.: "Specific Covalent Labelling of Recombinant Protein Molecules Inside Live Cells", Science 281, pp. 269-271 (1998); DOI: 10.1126/science.281.5374.269.

Adams et al.: "New Biarsenical Ligands and Tetracysteine Motifs for Protein Labeling in Vitro and in Vivo: Synthesis and Biological Applications"; JACS Articles; J. Am. Chem. Soc. 2002, 124, pp. 6063-6076.

McCann et al.: "Peptide tags for labeling membrane proteins in live cells with multiple fluorophores"; Harvard University, Cambridge, MA, USA; BioTechniques vol. 38, No. 6, pp. 945-952 (Jun. 2005).

Juillerat et al.: "Directed Evolution of $O^6$-Alkylguanine-DNA Alkyltransferase for Efficient Labeling of Fusion Proteins with Small Molecules In Vivo"; Chemistry & Biology, vol. 10, pp. 313-371, Apr. 2003.

Gautier et al.: "An Engineered Protein Tag for Multiprotein Labeling in Living Cells"; Chemistry & Biology, 15, pp. 128-136, Feb. 2008.

Gronemeyer et al.: "Directed evolution of $O^6$-alkylguanine-DNA alkyltransferase for applications in protein labeling"; Protein Engineering, Design & Selection, vol. 19, No. 7, pp. 309-316 (2006).

George et al.: "Specific Labeling of Cell Surface Proteins with Chemically Diverse Compounds"; JACS Communications; J. Am. Chem. Soc. 2004, 126, pp. 8896-8897.

González-Maeso et al.: "Identification of a serotonin/glutamate receptor complex implicated in physhosis"; Nature Publishing Group; vol. 452, Mar. 2008, doi:10.1038/nature06612, pp. 93-99.

Jianfeng et al., "Molecular Determinants Involved in the Allosteric Control of Agonist Affinity in the $GABA_B$ Receptor by the $GABA_{B2}$ Subunit*", The Journal of Biological Chemistry vol. 279, No. 16, Issue of Apr. 16, 2004, (pp. 15824-15830), XP002556320.

J.-P, Pin et al. "The activation mechanism of class-C G-protein coupled receptors." Biology of the Cell/Under the Auspices of the European Cell Biology Organization, vol. 96, No. 5, Received Jan. 14, 2004 accepted Mar. 11, 2004 Available on line Apr. 16, 2004 www.elsevier.com/locate/biocell, (pp. 335-342), XP002556319.

Imbert et al., "Recommendations for the Reduction of Compound Artifacts in Time-Resolved Fluorescence Resonance Energy Transfer Assays", Assay and Drug Development Technologies, LNKD-PUBMED: 17638536, vol. 5, No. 3, Jun. 2007, (pp. 363-372), XP002593112.

Maurel D et al., Cell-surface protein-protein interaction analysis with time-resolved FRET and snap-tag technologies: application to GPCR oligomerization, Nature Methods 200806 GB, vol. 5, No. 6, Jun. 2008, (pp. 561-567), XP002556321.

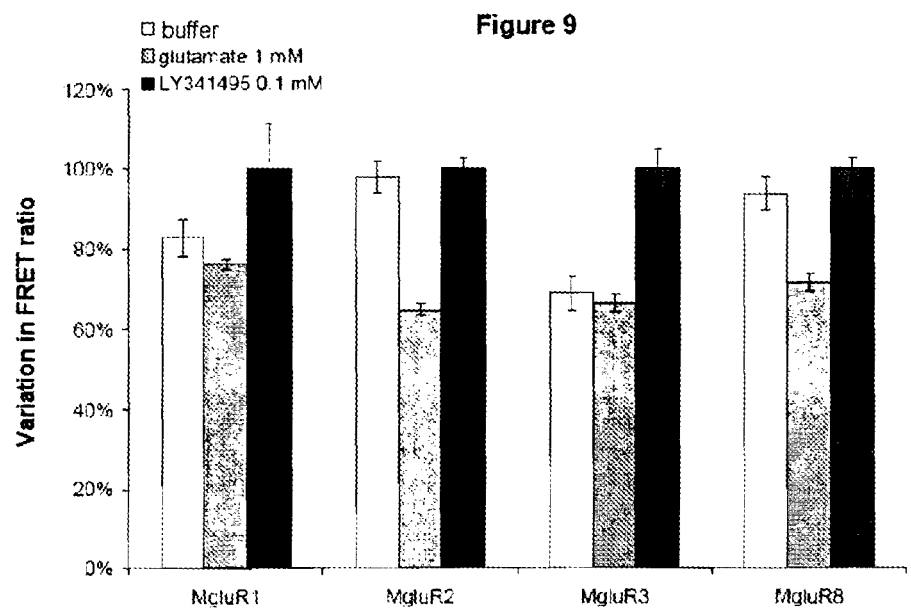
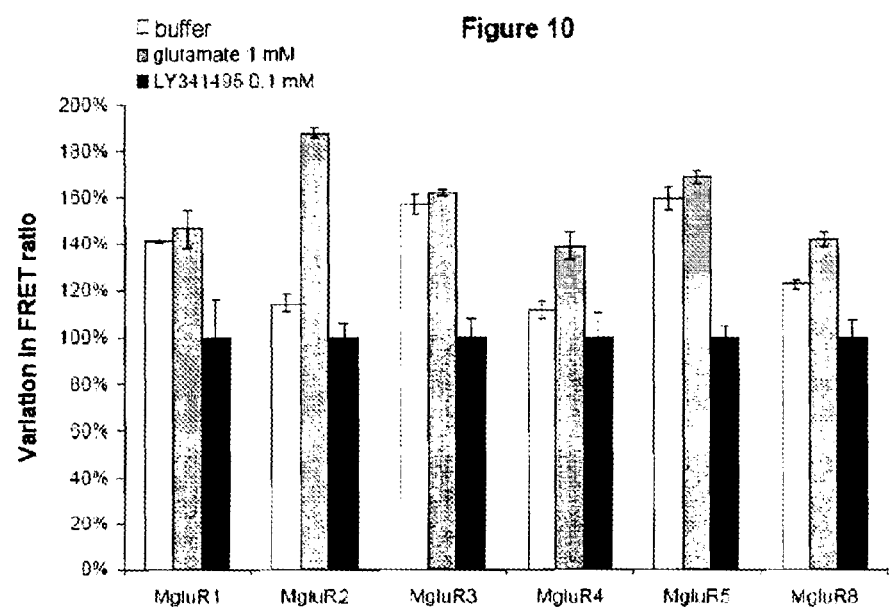

METHOD FOR DETECTING COMPOUNDS MODULATING DIMERS OF VFT DOMAIN MEMBRANE PROTEINS

This application is a 371 of PCT/FR10/50814, filed Apr. 29, 2010, which claims the priority of France 0952908, filed Apr. 30, 2009.

PRIOR ART

The invention relates to compounds modulating membrane receptors which are of interest in the search for new medicaments and for new taste modulators and in agriculture.

G-protein coupled receptors (GPCRs) constitute the largest family of mammalian membrane receptors since they represent 3.4% of the genome. The isolation and then the cloning of GPCRs have made it possible to identify, in humans, around 900 genes, of which approximately 500 correspond to olfactory and taste receptors and 400 to receptors capable of binding endogenous ligands. Thus, the heterogeneity of these receptors provides a very broad recognition of both external signals (odors, light, taste molecules) and internal signals (hormones and neurotransmitters).

GPCRs are referenced in three major classes:

Class A, with rhodopsin being the archetype, is the most widely represented class. The binding site for the ligands of these receptors involves mainly the transmembrane domains and also the extracellular loops of the GPCRs.

GPCR class B is characterized by a broad extracellular N-terminal domain (between 100 and 500 amino acids) containing conserved cysteines that are involved in disulfide bridges. The ligands of these receptors bind exclusively to the extracellular domains (N-terminal domain and GPCR extracellular loops).

The class C receptors are characterized by a very large extracellular domain (~600 amino acids) resembling bacterial periplasmic proteins, involved in the transport of amino acids, sugars and ions, called VFT (acronym of Venus Fly-Trap) domain. They comprise the metabotropic glutamate receptors (mGluR1, mGluR2, mGluR3, mGluR4, mGluR5, mGluR6, mGluR7 and mGluR8 receptors), the gamma-aminobutyric acid or GABA receptor ($GABA_B$ receptor) the sweet taste receptor and the umami taste receptor, the extracellular calcium-sensing receptor (CaSR) and also a basic amino acid receptor (GPRC6a). Other class C GPCRs comprising a VFT domain exist in the animal world, in particular the V2R pheromone receptors.

It is commonly accepted that all class C GPCRs comprising a VFT domain are dimeric, i.e. they are composed of two subunits and the association of the two subunits is essential to the functioning of the receptor. Some are homodimeric, consisting of two identical subunits (the mGluR, CaSR and GPRC6A receptors), while the others are heterodimeric, consisting of subunits resulting from the expression of distinct genes (the $GaBA_B$ receptor with the two subunits GB1 and GB2, the sweet taste receptor with TAS1R2 and TAS1R3, the umami taste receptor, with TAS1R 1 and TAS1R3).

In the case of class C GPCRs, comprising a VFT domain, each subunit has, in its N-terminal portion, a broad extracellular domain, responsible for the binding of the orthosteric ligand, and called the "Venus Flytrap" domain or VFT domain. The VFT domains are conserved protein domains that are present in class C GPCRs, and also in some other receptors, in particular the ionotropic glutamate receptors commonly called AMPA, NMDA or Kainate receptors, the receptors of the atrial natriuretic peptide receptor family (NPR-A and NPR-B) and the venus-kinase receptor (VKR) which is present in insects.

The VFT domains of these receptors share a characteristic structure in the form of a clam shell, with two lobes arranged around a hinge and making a crevice in which the orthosteric ligand binds. The flexibility of the hinge enables the two lobes to close in response to the binding of the activating ligand. The closing of the VFT domain by the orthosteric ligand is the first step essential to activation of the receptor. Conversely, antagonist ligands keep the VFT domain in an open position and the receptor in an inactivated state.

Within a dimeric receptor, the VFT domains of the two subunits are organized as a dimer of VFT domains, as illustrated by the X-ray crystallographic structure obtained on the dimer of VFT domains of the mGluR1 receptor (Kunishima et al., Nature. 2000 Oct. 26; 407(6807):971-7.; Tsuchiya et al., Proc Natl Acad Sci USA. 2002 Mar. 5; 99(5):2660-5). The model for activation of class C GPCRs comprising a VFT domain suggests that the binding of an activating ligand causes not only the closing of at least one VFT, but also a change in orientation of one VFT relative to the other. This relative movement results in the two C-terminal ends of the VFTs moving closer together, which is apparently itself responsible for the change in conformation of the membrane domains that is necessary for the recruitment of the G protein and for the signal transduction.

The class C GPCRs comprising a VFT domain are extremely important targets in the search for novel medicaments. mGluR receptors are implicated in particular in Parkinson's disease, schizophrenia, pain; the $GABA_B$ receptor plays a role in epilepsy and drug-dependence phenomena; the CaSR receptor is implicated in osteoporosis. These receptors are also of interest in the search for new sweet taste molecules (sweet taste receptor) or else new flavor enhancers (umami taste receptor). Finally, the search for V2R pheromone receptor modulators is of interest in the agricultural field.

Screening techniques exist which make it possible to follow the binding of a ligand and/or the activation of the GPCR subsequent to the binding of the ligand: GTP-gammaS (radioactive), electrophysiology, use of radioactive ligands. These screening methods cannot be used on a large scale.

High-throughput screening platforms generally use mammalian cells that have been stably or transiently transfected so as to express the receptor of interest. The action of a test compound is identified by means of functional tests based on the detection of a variation in the intracellular concentration of secondary messengers appearing in the cell after the activation of G-proteins coupled to said receptor. The secondary messenger measured depends on the type of G-protein coupled to the receptor of interest:

Gs-protein coupled receptors: the accumulation of the second messenger cAMP is measured in order to characterize the pharmacological action on a GPCR coupled to a Gs protein.

Gq-protein coupled receptors (this is the case of the glutamate receptors mGluR1 and mGluR5, of the extracellular calcium receptor CaSR, and of the basic amino acid receptor GPRC6A): the accumulation of an IP3 metabolite, for example IP1. Alternatively, by loading the cells with a fluorescent calcium probe, it is possible to visualize the transient increase in intracellular calcium concentration.

Gi-protein coupled receptors (examples: the glutamate receptors mGluR2, mGluR3, mGluR4, mGluR6, mGluR7 and mGluR8, the GABA receptor $GABA_B$, and the sweet taste and umami taste receptors): indirectly, the receptor is stimulated with forskolin or isoproterenol, which causes an increase in cAMP concentration. The inhibition of this increase by a compound tested is representative of the coupling of the receptor with the Gi protein. Another possibility, which is generally preferred for screening, is to coexpress the receptor of interest with a chimeric G protein, resulting from the fusion of a part of the Gi protein, capable of recognizing the GPCR in its activated state, and of a part of the Gq protein, capable of triggering the IP3/Ca$^{2+}$ pathway. Under these conditions, the activation of the receptor can be detected by the transient calcium signal which occurs.

The existing techniques are poorly suited to demonstrating compounds capable of modulating the activation of dimeric class C GPCRs: agonist effects are very difficult to detect when the receptors have a weak affinity for their natural ligand (this is the case of the mGlu receptors); functional tests based on measuring a secondary message resulting from the signal transduction inside the cell (cAMP, 1P3, IP1) are also not suitable from the viewpoint of the relative difficulty in implementing them and of the complexity of the effector pathways coupled to dimeric receptors. FRET (Förster resonance energy transfer) techniques based on the expression of GPCRs fused at their intracellular (C-terminal) domains with fluorescent proteins are also not suitable owing to the high background noise that comes from the dimers present in the intracellular compartments. U.S. Pat. No. 6,824,990 describes, generally, methods for studying the dimerization of GPCRs based on labeling GPCRs capable of forming dimers, with energy donor and acceptor compounds, in particular fluorescent proteins, and measuring FRET variation. This patent does not describe a technical solution which makes it possible to select compounds modulating class C GPCR dimers. Moreover, it is essentially illustrated through the use of fluorescent proteins which are not very suitable in the present case owing to the high background noise generated by the dimers present in the various intracellular compartments.

Maurel et al. (Nat. Methods; June 2008; 5(6):561-7) applied the FRET technique to the study of GABA receptor dimers: they labeled each of the GABA$_{B1}$ and GABA$_{B2}$ subunits of the GABA$_B$ receptor with a europium cryptate (Eu-Pyridine-bis-bipyridine) and an acceptor fluorophore (d2). These studies did not make it possible to observe any variation in FRET signal when the receptor is activated by its agonist, GABA, and suggest that this approach is not suitable for studying these dimers.

The present invention proposes to provide a method and products for demonstrating compounds having a modulating effect on the activation state of dimers of membrane proteins comprising a VFT domain, in particular class C GPCRs, making it possible to determine whether test compounds have a pharmacological effect on these receptors.

This invention is of particular importance since, at the current time, there are no techniques which make it possible to efficiently and easily screen for dimeric receptors of this type in order to find new medicaments.

DESCRIPTION OF THE FIGURES

FIG. 9 represents the variation in the ratio of FRET emitted by the mGluR1-mGluR1, mGluR2-mGluR2, mGluR3-mGluR3 and mGluR8-mGluR8 dimers in the presence of glutamate or of LY341495, or in the absence of these compounds.

FIG. 10 represents the variation in the ratio of FRET emitted by the mGluR1-mGluR1, mGluR2-mGluR2, mGluR3-mGluR3, mGluR4-mGluR4, mGluR5-mGluR5 and mGluR8-mGluR8 dimers, in the presence of glutamate or of LY341495, or in the absence of these compounds.

CRD domain, ending after the amino acids LPQEY—SEQ ID No. 8), fused to the Snap-tag protein (S), and (ii) the first 414 amino acids (without methionine 1) of the short variant of the D2 dopaminergic receptor, corresponding to its transmembrane domain.

Figure 14:
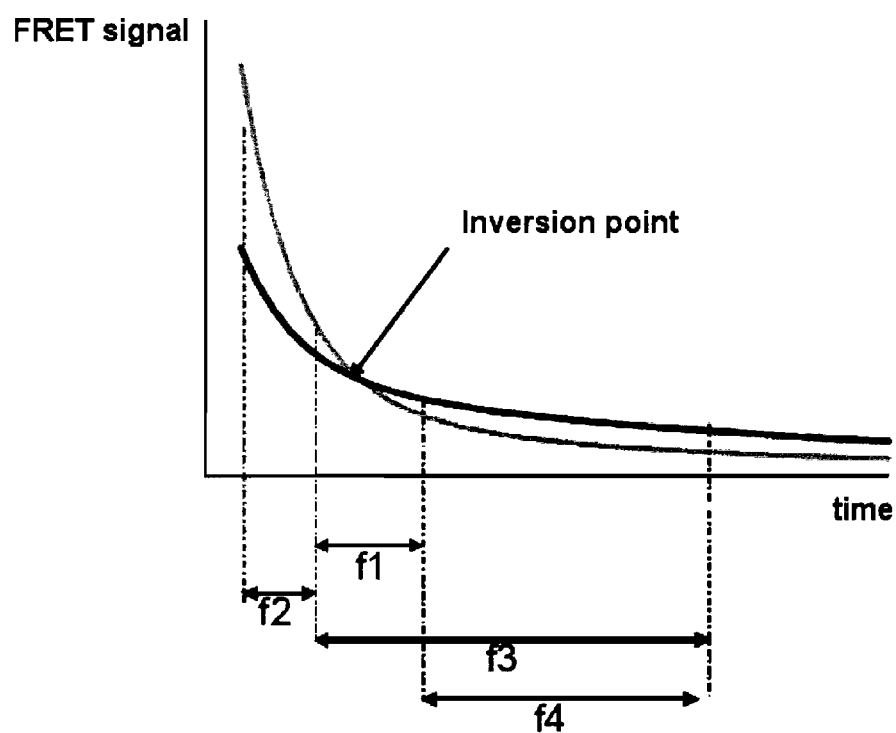

FIG. 14 represents the variation in FRET signal as a function of time.

DESCRIPTION

The invention relates to a method for selecting compounds having a modulating effect on the activation state of a dimer of VFT-domain proteins expressed in cell membranes present in a measuring medium, said dimer consisting of a first protein and of a second protein, said proteins being identical or different, wherein the method comprises the following steps:
(a) labeling the first and second protein in the N-terminal portion of their VFT domains with the members of a pair of FRET partners;
(b) exciting the FRET partners and measuring the FRET signal in the absence and in the presence of a test compound;
(c) selecting the test compound as a modulating compound if a difference in FRET signal in the absence and in the presence of a test compound is measured in step (b).

Surprisingly, the inventors have demonstrated that the absence of variation in FRET signal in the presence of a modulator of the activity of dimers of VFT-domain proteins, observed in the prior art by Maurel et al., is linked to the choice of the time window in which the signal is measured. FRET signals are conventionally measured after a delay following light excitation of the measuring medium, and for a predetermined period (the integration time). The products and instruments available for carrying out biological assays based on measuring FRET signals are designed so as to avoid the user varying this signal-measuring time window.

In the case of dimers of VFT-domain proteins, the inventors have discovered that, when the decrease in FRET signal over time is measured in the presence or in the absence of a reference agonist compound, an inversion point is observed, corresponding to the time after excitation at which the FRET values in the presence and in the absence of this reference agonist compound are identical.

The inventors have determined that, before this inversion point, the FRET signal in the absence of a reference agonist compound (gray curve in FIG. 14) is higher than that measured in the presence of agonist (black curve in FIG. 14). From the inversion point onward, the FRET signal observed in the absence of agonist becomes, on the contrary, lower than that measured in the presence of agonist.

Moreover, if the signal is measured in certain time windows comprising the inversion point (for example f1, cf. FIG. 14), no variation in FRET signal in the presence or in the absence of modulating compound is observed. In other words, the inventors have identified the problem explaining the absence of variation in FRET signal observed in the prior art, namely the existence of an inversion point in the time window used in the past.

It follows from this discovery that, when the FRET signal is measured in a time window located before or after this inversion point (f2, f4, cf. FIG. 14), the FRET signals measured in the presence and in the absence of reference agonist compound will always be different. It is possible to choose a time window comprising the inversion point (f3, cf. FIG. 14), but in this case, it will be necessary to be sure that the signals measured in the presence and in the absence of a reference agonist or antagonist compound are different.

The invention therefore consists of a method for selecting compounds having a modulating effect on the activation state of a dimer of VFT-domain proteins expressed in cell membranes present in a measuring medium, said dimer consisting of a first protein and of a second protein, said proteins being identical or different, wherein the method comprises the following steps:
(a) labeling the first and second protein in the N-terminal portion of their VFT domains with the members of a pair of FRET partners;
(b) exciting the FRET partners and measuring the FRET signal in the absence and in the presence of a test compound;
(c) selecting the test compound as a modulating compound if a difference in FRET signal in the absence and in the presence of a test compound is measured in step (b), the FRET signal being measured in step (b) within a time window in which the signals measured in the presence and in the absence of a reference agonist or antagonist compound are different.

It is considered that the signals measured in the presence and in the absence of a reference agonist or antagonist compound are different if one of the following conditions is met:
if there is a difference of more than 20% between the mean values of the signals in the presence and in the absence of reference agonist compound, or else
if the mean values of the signals in the presence and in the absence of agonist compound differ by more than three times the highest standard deviation (either the standard deviation of the signal measured in the absence of reference agonist, or that of the signal measured in the presence of this compound).

The time window can be determined experimentally by varying the delay before the signal is measured after excitation and the period during which this signal is measured (integration time). These parameters can be easily modified with the commercially available fluorimeters.

In one particular implementation, the method according to the invention is characterized in that the signal measured in step (b) is done so with a delay of between 180 and 800 µs after excitation and an integration time of from 200 to 2000 µs.

In another particular implementation, the method according to the invention is characterized in that:
(i) either the Förster radius ($R_0$) of said pair of FRET partners is between 20 and 55 Å, and the signal measured in step (b) is done so with a delay of between 10 and 100 µs after excitation and an integration time of from 100 to 500 µs;
(ii) or the Förster radius ($R_0$) of said pair is greater than 55 Å, and the signal measured in step (b) is done so with a delay of between 180 and 800 µs after excitation and an integration time of from 200 to 2000 µs.

The method of the invention makes it possible, relatively simply, to screen large libraries of compounds in order to evaluate their effects on membrane proteins comprising a VFT domain, and in particular class C GPCRs comprising a VFT domain which represent a target of choice in particular for discovering new medicaments.

The method according to the invention can thus be implemented for discovering new modulators of metabotropic glutamate receptors (consisting of dimers of subunits chosen from: mGluR1, mGluR2, mGluR3, mGluR4, mGluR5, mGluR6, mGluR7, mGluR8), of the gamma-aminobutyric acid or GABA receptor ($GABA_B$ receptor consisting of one GB1 subunit and one GB2 subunit), of receptors associated with the perception of the sweet taste (TAS1R1-TAS1R3 dimer) or of the umami taste (TAS1R2-TAS1R3 dimer), of the extracellular calcium-sensing receptor (homodimer of CaSR subunits) and of the basic amino acid receptor (homodimer of GPRC6a subunits). These terms encompass the wild-type forms of these receptors, and also mutant, truncated, chimeric or modified forms as described hereinafter.

The method according to the invention is preferentially implemented with metabotropic glutamate receptors or with taste receptors.

When the method according to the invention is implemented on glutamate receptors, the latter may consist of the following dimers: mGluR1-mGluR1; mGluR1-mGluR2; mGluR1-mGluR3; mGluR1-mGluR4; mGluR1-mGluR5; mGluR1-mGluR6; mGluR1-mGluR7; mGluR2-mGluR2; mGluR2-mGluR3; mGluR2-mGluR4; mGluR2-mGluR5; mGluR2-mGluR6; mGluR2-mGluR7; mGluR3-mGluR3; mGluR3-mGluR4; mGluR3-mGluR5; mGluR3-mGluR6; mGluR3-mGluR7; mGluR4-mGluR4; mGluR4-mGluR5; mGluR4-mGluR6; mGluR4-mGluR7; mGluR5-mGluR5; mGluR5-mGluR6; mGluR5-mGluR7; mGluR6-mGluR6; mGluR6-mGluR7; mGluR7-mGluR7; mGluR8-mGluR1; mGluR8-mGluR2; mGluR8-mGluR3; mGluR8-mGluR4; mGluR8-mGluR5; mGluR8-mGluR6; mGluR8-mGluR7; mGluR8-mGluR8. In one particularly preferred implementation, the dimer is chosen from: an mGluR1 homodimer, an mGluR2 homodimer, an mGluR3 homodimer, an mGluR4 homodimer, an mGluR5 homodimer, an mGluR8 homodimer, an mGluR2-mGluR3 heterodimer and an mGluR2-mGluR4 heterodimer.

As regards the taste receptors, the dimer may be chosen from the dimers: TAS1R2-TAS1R3 or TAS1R1-TAS1R3.

Figure 13A:
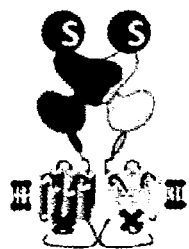
FIG. 13A represents a dimer of mGluR2, each one conjugated to the Snap-tag enzyme (S), and comprising the mutation F756P which prevents their coupling with G proteins.
Figure 13B:
FIG. 13B represents a dimer of mGluR2, each one conjugated to the Snap-tag enzyme (S), and comprising the mutation F756P which prevents their coupling with G proteins, and also the mutation C234A which renders these proteins insensitive to the allosteric modulators.
Figure 13C:
FIG. 13C represents a dimer of mGluR2, each one truncated from amino acid 597 (middle of the first intracellular loop i1), fused to the Snap-tag enzyme (S), and therefore comprising just one transmembrane domain, a CRD domain and an VFT domain.

The method according to the invention may be implemented with dimers of proteins corresponding to truncated GPCRs, for example proteins truncated in the first intracellular loop and therefore containing just one transmembrane domain (FIG. 13C). The splice variants of VFT-domain proteins not comprising transmembrane domains (Ferraguti et al., Cell Tissue Res. 2006 November; 326(2):483-504) can also be used, with the proviso that, when such a variant constitutes one of the subunits of the dimer studied, the other subunit comprises at least one transmembrane domain.

Figure 13D:
FIG. 13D represents a dimer of mGluR2, each one truncated after amino acid 561 (therefore comprising only a VFT domain and a CRD domain), fused to the Snap-tag enzyme (S), and into which a GPI anchor signal peptide (RRSSSTV-LFSSPVILLISFLIFLIVG—SEQ ID No. 7) has been inserted after the cysteine-rich domain (CRD, i.e. after the amino acids LPQEY—SEQ ID No. 8).
Figure 13E:
FIG. 13E represents a dimer of mGluR2, each one truncated from amino acid 499 (therefore comprising only a VFT domain), fused to the Snap-tag enzyme (S), and into which a GPI anchor signal peptide (RRSSSTVLFSSPVILLIS-FLIFLIVG—SEQ ID No. 7) has been inserted after the VFT domain (i.e. after the amino acids GPLPAS—SEQ ID No. 9).
Figure 13F:
FIG. 13F represents a dimer of chimeric receptors each comprising (i) the first 561 amino acids of mGluR2 (VFT+

The method according to the invention can also be implemented with chimeric receptors comprising an extracellular domain of a VFT-domain receptor, and one or more transmembrane domains of other receptors (see FIG. 13F). Such chimeric receptors can be produced by conventional molecular biology techniques consisting in producing expression vectors containing the DNA encoding the domains in question, the nucleic sequences of which are available, for example, in the Genbank database, and in transfecting these vectors into cells. Malitschek et al. (Mol Pharmacol. 1999 August; 56(2):448-54) have described such chimeric receptors.

The method according to the invention can also be implemented with protein constructs comprising an extracellular domain of a VFT-domain receptor and a glycosylphosphatidylinositol anchor ("GPI anchor") in place of a transmembrane domain, which will make it possible to anchor the protein portion at the surface of the plasma membrane (see FIGS. 13D and 13E). Such proteins and the production thereof are described in particular by Liu et al. (J Biol Chem. 2004 Apr. 16; 279(16):15824-3).

In another particular implementation of the invention, the dimers used are mutant GPCRs which are not coupled to any intracellular signaling pathway. These mutant GPCRs are known, and comprise, for example, GPCRs containing one or more mutations preventing coupling with G proteins, such as the F756P mutant of mGluR2 (see FIG. 13A). This implementation is preferred when the dimers are stably expressed by the cell, which can have a toxic effect on the cell.

It may also be advantageous to use dimers consisting of GPCRs containing a mutation which makes them insensitive to the effect of allosteric modulators, for instance the C234A mutant of mGluR2 (FIG. 13B). The use of such mutants for implementing the invention makes it possible to discover modulating compounds which are not allosteric modulators.

Finally, the method according to the invention can also be implemented with other VFT-domain receptors which are not class C GPCRs, in particular ionotropic glutamate receptors (commonly called AMPA, NMDA or Kainate receptors), receptors of the atrial natriuretic peptide receptor family (NPR-A and NPR-B) and the venus-kinase receptor (VKR) which is present in insects.

DEFINITIONS

"Pair of FRET partners": This expression denotes a pair consisting of an energy donor fluorescent compound (hereinafter "donor fluorescent compound") and an energy acceptor compound (hereinafter "acceptor compound"); when they are close to one another and when they are excited at the excitation wavelength of the donor fluorescent compound, these compounds emit a FRET signal. It is known that, in order for two fluorescent compounds to be FRET partners, the emission spectrum of the donor fluorescent compound must partially overlap the excitation spectrum of the acceptor compound.

"FRET signal": Denotes any measurable signal representative of a FRET between a donor fluorescent compound and an acceptor compound. A FRET signal can therefore be a variation in the intensity or in the lifetime of luminescence of the donor fluorescent compound or of the acceptor compound when the latter is fluorescent.

"Time window": Denotes the period of time which begins when the FRET signal is measured after a delay following the light excitation of the measuring medium and ends at the end of the integration time. For example, a "50-450 µs" time window means that the FRET signal is measured after a delay of 50 µs after light excitation of the measuring medium, for a period (integration time) of 400 µs.

"Measuring medium": Denotes the content of the well of a plate, of a test tube or of any other container suitable for mixing cells or cell membranes with the reagents necessary for implementing the invention.

"Modulating compound": The expression "compounds having a modulating effect on the activation state of dimers of VFT-domain proteins" is intended to mean compounds having an activating or deactivating effect.

The activating compounds can in particular be agonist compounds, partial agonists or positive allosteric modulators. The effect of the positive allosteric modulator compounds is visible only on dimers activated by one of their reference agonists: in this case, the positive allosteric modulators will cause an increase in the activation of the receptor. In the absence of reference agonist, the effect of the positive allosteric modulator is not visible.

The deactivating compounds decrease the activity of the dimers and are either inverse agonists, in the case where they have a deactivation effect on a constitutively active dimer, or negative allosteric modulators or antagonists when they lead to deactivation of the dimer previously activated by one of its reference agonists.

The modulating compounds are added to the measuring medium and their effect on the activation state is observed according to the method of the invention. There is no limitation as to the chemical nature of these modulating compounds, nor as to their mode of action: the invention in fact makes it possible to detect changes in conformation in the VFT domains, these changes resulting from the binding of the modulating compounds to either or both of the constituent subunits of the dimer, but also to other membrane proteins that will themselves exert an effect on the VFT-domain dimer of interest.

According to one particular implementation, the method according to the invention comprises the following steps:
(a) labeling the first and second protein in the N-terminal portion of their VFT domains with the members of a pair of FRET partners, the Förster radius (R0) of said pair being between 20 and 55 Å;
(b) measuring the FRET signal in the absence and in the presence of test compound;
(c) selecting the test compound as a modulating compound by comparing the variation in FRET signal in the presence or in the absence of said test compound with that measured in the presence or in the absence of a known modulating compound for said dimer.

In this particular implementation, the FRET signal is advantageously measured in step (b) with a delay of 50 μs after excitation and an integration time of 450 μs.

Depending on the nature of the known modulator of the dimer and the variation in FRET signal measured in the presence or in the absence of test compound compared with that observed in the presence or in the absence of said known modulating compound, the nature of the test compound is determined.

Thus, if the known modulator of the dimer is an agonist, the test compound will be an activating compound if the variation in FRET signal measured in the presence and in the absence of said test compound is in the same direction as that observed in the presence of a known agonist compound, and a deactivating compound if said variation in FRET signal is in the opposite direction to that observed in the presence and in the absence of said known agonist compound.

Likewise, if the modulator of the dimer is a known antagonist of said dimer, the test compound will be an activating compound if the variation in FRET signal measured in the presence and in the absence of test compound is in the opposite direction to that observed in the presence and in the absence of said known antagonist compound, and an activating compound if said variation in FRET signal is in the same direction as that observed in the presence and in the absence of said known antagonist compound.

In practice, the dose-response curves for the test compound can be compared with those obtained with a known agonist or antagonist compound.

It should be noted that, in certain cases, the measurements of FRET signal with or without test compound can be carried out in the presence of a given amount of a reference agonist compound. This is in particular the case when positive or negative allosteric modulators or antagonists are sought. This is of course not necessary when agonist or partial agonist compounds are sought.

In the particular case of the implementation of the method according to the invention with dimers of metabotropic glutamate receptors (mGluR), and when the signal is measured with a delay of 50 μs after excitation and an integration time of 450 μs, the inventors have discovered that:
the addition to the measuring medium of a compound that is an agonist of the mGluR dimer studied causes a decrease in the FRET signal emitted, relative to that observed in the absence of this compound; in the case of a partial agonist, i.e. the effect of which is not as great as that of the "natural" agonist, this decrease is of a lesser intensity;
the addition to the measuring medium of a compound that is an antagonist of the mGluR dimer studied causes an increase in the FRET signal emitted, relative to that observed in the absence of this compound. This effect can be observed on constitutively active dimers or else on dimers activated by an agonist compound;
the addition to the measuring medium of a modulator with a positive allosteric effect causes a decrease in the FRET signal emitted, relative to that observed in the absence of such a modulator. This effect can be observed only in the presence of agonist in the measuring medium, for example the natural agonist of the receptor studied;
the addition to the measuring medium of a modulator with a negative allosteric effect causes an increase in the FRET signal emitted, relative to that observed in the absence of such a modulator. This effect can be observed only in the presence of agonist in the measuring medium, for example the natural agonist of the receptor studied.

Conversely, when the signal is measured with a longer delay, for example with a delay of 500 μs after excitation, and an integration time of 500 μs, the inventors have discovered that the signal measured after the addition to the measuring medium of a compound that is an agonist of the mGluR dimer is greater than that measured in the absence of this compound.

It is important to note that the method according to the invention also makes it possible to demonstrate compounds having a transregulating effect, i.e. compounds which do not bind to the dimer of VFT-domain proteins, but to another membrane receptor which will itself interact with the dimer in question: the mGluR2 receptor, for example, can be regulated by the 5HT2A serotonin receptor (Gonzalez-Maeso et al., Nature, Vol. 452, March 2008 93-99) and the method according to the invention makes it possible to demonstrate this type of modulation of the mGluR2 dimer.

The method according to the invention therefore makes it possible to demonstrate compounds which do not bind to the dimer studied, but to another membrane protein which plays a regulating (activating or inhibiting) role on said receptor. It is thus possible to demonstrate compounds having an indirect activating or deactivating effect on said receptor.

Cell Membranes Comprising Dimers of VFT-Domain Proteins

The method according to the invention is implemented in a measuring medium containing cell membranes which contain the dimers of VFT-domain proteins. The measuring medium therefore comprises, at the time of the addition of the FRET partner compounds, either live intact cells, which are adherent or in suspension, or preparations of cell membranes in suspension, obtained for example by cell lysis and fractional centrifugation. The techniques for preparing membrane suspensions are known to those skilled in the art. The method according to the invention is preferably implemented on live intact cells.

The dimers of transmembrane proteins comprising a VFT domain are expressed in the cell membranes naturally by the cells, or else are expressed using conventional molecular biology techniques, via expression vectors introduced stably or transiently into the cells. The reagents intended for stably or transiently producing heterologous DNA in cells are commercially available, and the DNA sequences encoding the transmembrane proteins comprising a VFT domain, in particular those encoding the class C GPCRs cited above, are available in the databases such as Genbank. As indicated above, when the dimers are expressed stably by the cells, it is advisable to use mutant GPCRs which are not coupled to any G protein, in order to avoid the possible toxic effects on the cell.

The Pair of FRET Partners

One of the essential characteristics of the invention is that each of the constituent proteins of the dimer studied is labeled with a member of a pair of FRET partners. In one preferred implementation of the method according to the invention, the Förster radius ($R_0$) of the pair of FRET partners is between 20 and 55 Å. In another preferred implementation, this radius is greater than 55 Å.

Those skilled in the art are capable of choosing, among the commercially available FRET partner compounds, those of which the Förster radius is included in these ranges. The Förster theory in fact teaches how to determine the value of $R_0$ for a given pair of FRET partners.

According to this theory, FRET is defined as a transfer of non-radiative energy resulting from a dipole-dipole interaction between an energy donor and an energy acceptor. This physical phenomenon requires energy compatibility between these molecules. This means that the emission spectrum of the donor must overlap, at least partially, the absorption spectrum of the acceptor. This overlapping of the spectra is defined by the overlap integral $J(\lambda)$:

$$J_{(\lambda)} = \int f_D(\lambda)\epsilon_A(\lambda)\lambda^4 d\lambda$$

where $f_p$ is the intensity of the fluorescence emitted by the donor at a given wavelength, and $\epsilon_A$ is the molar extinction coefficient of the acceptor. The factor J therefore reflects the capacity of a pair of fluorophores to emit and absorb energy at the same wavelength. In accordance with the Förster theory, FRET is a process which depends on the distance separating the two molecules, donor and acceptor, as shown by the following formula:

$$E = \frac{1}{1 + (R/R_0)^6}$$

where R is the effective distance which separates the two molecules and $R_0$ is the Förster radius. The latter corresponds to the donor/acceptor distance for which the efficiency of the energy transfer is 50%. The mathematical expression for calculating this distance is:

$$R_0 = (10^{-3}\kappa^2 n^{-4} Q_D J)^{1/6} \times 9730$$

where J is the overlap integral, n the refractive index of the medium ($n^{-4}$ is generally between ⅓ and ⅕), $Q_D$ is the quantum yield of the donor in the absence of acceptor and $\kappa^2$ is the orientation factor which depends on the relative orientation of the dipoles of the donor and of the acceptor. Even though the value of $\kappa^2$ is theoretically between 0 and 4, ⅔ is the value normally used for determining $R_0$. Indeed, $\kappa^2$ is considered to be ⅔ when the donor and the acceptor have a degree of freedom that is sufficient to be randomly oriented in space. This condition is generally met for fluorophores attached to biomolecules since they can have a certain freedom of rotation.

An example of a calculation of $R_0$ for the pair europium pyridine-bis-bipyridine cryptate and d2 (a fluorophore sold by the company Cisbio Bioassays) is detailed by Maurel et al. (Nature methods 2008, supplementary figures and texts). In this example, $R_0$ is 65.5 Å.

Many energy donor or acceptor compounds have been described and are commercially available.

The fluorescent compounds can be chosen from the following group: allophycocyanins, in particular the one known under the trade name XL665; luminescent organic molecules, such as rhodamines, cyanins, squaraines, coumarins, proflavins, acridines, fluoresceins, the fluorophores known under the name Bodipy, the fluorophores known under the name Atto, the fluorophores known under the name Dy, the compounds known under the name AlexaFluor, nitrobenzoxadiazole, fluorescent metal complexes, such as rare earth cryptates, rare earth chelates (in particular chelates and cryptates of europium, of terbium, of samarium, of dysprosium or of neodymium); luminescent inorganic particles such as nanocrystals (quantum dots). These fluorescent compounds can be used either as donor fluorescent compounds or as acceptor fluorescent compounds in a FRET system.

The use of fluorescent proteins as an acceptor compound is possible. On the other hand, the use of these proteins as a donor is not recommended since these proteins would cause a significant increase in the background noise coming from the various cell compartments in which these proteins are expressed before they are targeted to the plasma membrane.

The following fluorescent proteins can be used according to the invention: cyan fluorescent proteins (AmCyan1, Midori-Ishi Cyan, mTFP1), green fluorescent proteins (EGFP, AcGFP, TurboGFP, Emerald, Azami Green, ZsGreen), yellow fluorescent proteins (EYFP, Topaz, Venus, mCitrine, YPet, PHiYFP, ZsYellow1, mBanana), orange and red fluorescent proteins (Orange kusibari, mOrange, tdtomato, DsRed, DsRed2, DsRes-Express, DsRed-Monomer, mTangerine, AsRed2, mRFP1, JRed, mCherry, mStrawberry, HcRed1, mRaspberry, HcRed-Tandem, mPlim, AQ143), and proteins that are fluorescent in the far-red range (mKate, mKate2, tdKatushka2).

Energy donor compounds with a long lifetime (>0.1 ms, preferably between 0.5 and 6 ms), in particular rare earth chelates or cryptates, are advantageous since they make it possible to carry out time-resolved measurements, i.e. to measure TR-FRET signals while doing away with a large part of the background noise emitted by the measuring medium. They are, for this reason, generally preferred for implementing the method according to the invention. Europium chelates or cryptates or terbium chelates or cryptates in particular are particularly suitable as energy donor member of the FRET pair.

Dysprosium (Dy3+), samarium (Sm3+), neodymium (Nd3+), ytterbium (Yb3+) or else erbium (Er3+) complexes are rare earth complexes that are suitable for the purposes of the invention, europium (Eu3+) complexes and terbium (Tb3+) complexes being particularly preferred.

A very large number of rare earth complexes have been described, and several are currently exploited commercially, in particular by the companies PerkinElmer, Invitrogen and Cisbio Bioassays.

Examples of rare earth chelates or cryptates that are suitable for the purposes of the invention are:

Rare earth cryptates comprising one or more pyridine units. Such rare earth cryptates are described, for example, in patents EP 0 180 492, EP 0 321 353, EP 0 601 113 and in international application WO 01/96877.
Terbium (Tb3+) and europium (Eu3+) cryptates are particularly suitable for the purposes of the present invention. Rare earth cryptates are sold by the company Cisbio Bioassays. Mention may be made, by way of nonlimiting example, of the europium cyptates having the formulae below (which can be coupled to the compound to be labeled via a reactive group, in this case for example an NHS group):

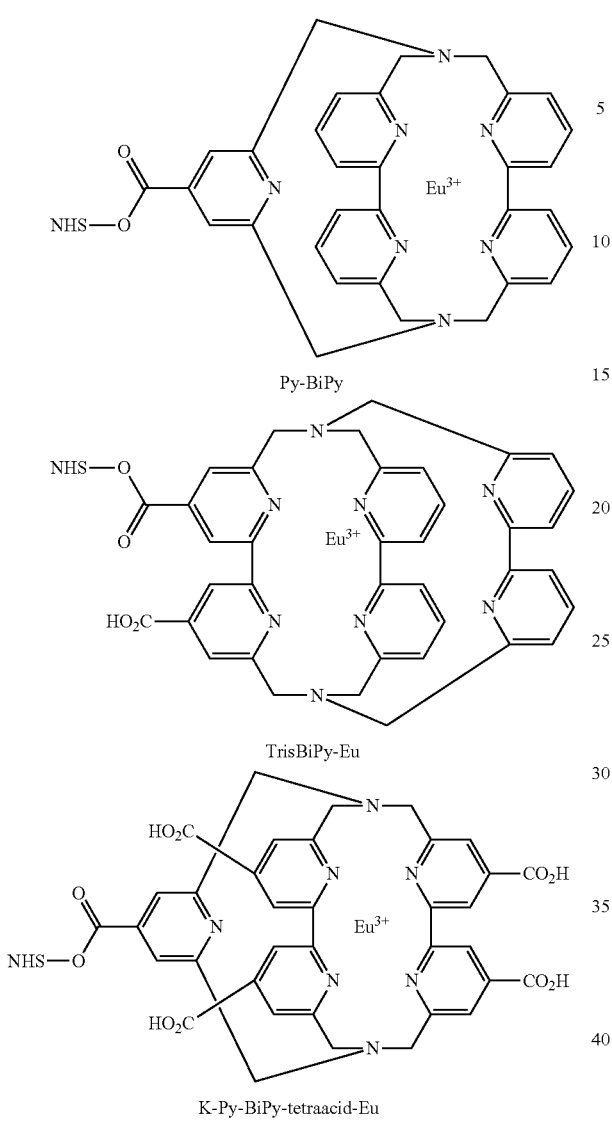

Py-BiPy

TrisBiPy-Eu

K-Py-BiPy-tetraacid-Eu

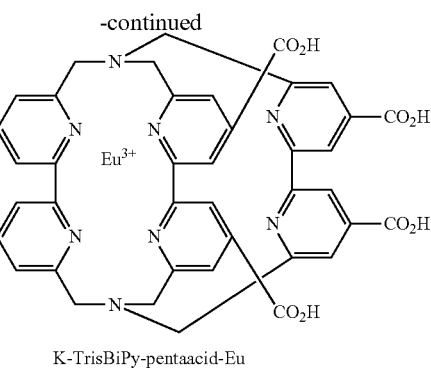

K-TrisBiPy-pentaacid-Eu

The Py-BiPy-tetraacid-Eu europium cryptate is particularly suitable for implementing the invention owing to its properties of resistance to fluorescence quenching in biological media.

The rare earth chelates described, in particular, in patents U.S. Pat. No. 4,761,481, U.S. Pat. No. 5,032,677, U.S. Pat. No. 5,055,578, U.S. Pat. No. 5,106,957, U.S. Pat. No. 5,116,989, U.S. Pat. No. 4,761,481, U.S. Pat. No. 4,801,722, U.S. Pat. No. 4,794,191, U.S. Pat. No. 4,637,988, U.S. Pat. No. 4,670,572, U.S. Pat. No. 4,837,169 and U.S. Pat. No. 4,859,777. Patents EP 0 403 593, U.S. Pat. No. 5,324,825, U.S. Pat. No. 5,202,423 and U.S. Pat. No. 5,316,909 describe chelates composed of a nonadentate ligand such as terpyridine. These rare earth chelates are sold by the company PerkinElmer.

Rare earth complexes consisting of a chelating agent, such as tetraazacyclododecane, substituted with a chromophore comprising aromatic rings, such as those described by Poole R. et al. in Biomol. Chem, 2005, 3, 1013-1024 "Synthesis and characterization of highly emissive and kinetically stable lanthanide complexes suitable for usage in cellulo", can also be used. The complexes described in application WO 2009/10580 can also be used.

The terbium cryptate Tb(KR) having the formula below (which can be coupled to the compound to be labeled via a reactive group, in this case for example an NHS group):

and the synthesis of which is described in international application WO 2008/063721 is one of the terbium cryptates most suitable for implementing the invention.

The terbium cryptate Lumi4-Tb from the company Lumiphore, sold by Cisbio Bioassays.

The "quantum dye" from the company Research Organics, having the formula below (which can be coupled to the compound to be labeled via a reactive group, in this case NCS):

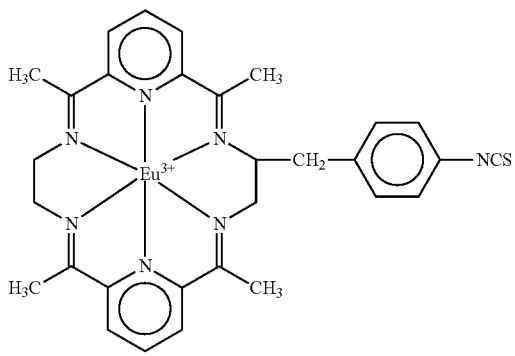

The terbium chelate DTPA-cs124 Tb, sold by the company Invitrogen, having the formula below (which can be coupled to the compound to be labeled via a reactive group R) and the synthesis of which is described in U.S. Pat. No. 5,622,821.

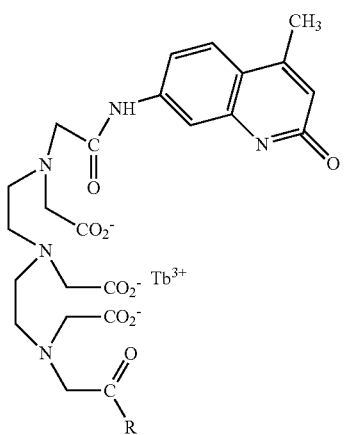

According to the donor chosen, and by applying the principles of the Förster theory summarized above, those skilled in the art are able to determine the Förster radius of the FRET partner pair to be used according to the invention.

By way of nonlimiting examples, the table hereinafter lists pairs of FRET partners of which the Förster radius is between 20 and 55 Å:

|  | Tb(KR) | DTPA-cs124 Tb | Lumi4-Tb |
|---|---|---|---|
| Atto425 | 21 Å | 21 Å | 21 Å |
| Alexa430 | 21 Å | 21 Å | 21 Å |
| Coumarin343 | 23 Å | 23 Å | 23 Å |
| Acridine orange | 26 Å | 26 Å | 26 Å |
| Lucifer yellow | 26 Å | 26 Å | 26 Å |
| Acridine yellow | 27 Å | 27 Å | 27 Å |
| proflavine | 29 Å | 29 Å | 29 Å |
| Atto465 | 30 Å | 30 Å | 30 Å |
| Nitrobenzoxadiazole | 33 Å | 33 Å | 33 Å |
| Courmarin 6 | 34 Å | 34 Å | 34 Å |
| Alexa 750 | 40 Å | 40 Å | 40 Å |
| Cy7 | 40 Å | 40 Å | 40 Å |
| Fluorescein | 46 Å | 46 Å | 46 Å |
| Nile red | 46 Å | 46 Å | 46 Å |
| Alexa488 | 46 Å | 46 Å | 46 Å |
| Dy495 | 46 Å | 46 Å | 46 Å |
| Dy490 | 46 Å | 46 Å | 46 Å |
| Oregon green | 47 Å | 47 Å | 47 Å |
| Atto488 | 47 Å | 47 Å | 47 Å |
| Atto495 | 47 Å | 47 Å | 47 Å |
| Alexa514 | 47 Å | 47 Å | 47 Å |
| Atto520 | 48 Å | 48 Å | 48 Å |
| Cy2 | 52 Å | 52 Å | 52 Å |
| Rhodamine6G | 53 Å | 53 Å | 53 Å |
| Alexa700 | 54 Å | 54 Å | 54 Å |
| Alexa680 | 55 Å | 55 Å | 55 Å |
| Atto532 | 55 Å | 55 Å | 55 Å |
| Alexa532 | 55 Å | 55 Å | 55 Å |
| EGFP | 45 Å | — | 45 Å |
| YFP | 43 Å | — | 43 Å |
| mPlum | 53 Å | — | 53 Å |

Among these pairs, the Tb(KR)/fluorescein and Lumi4-Tb/fluorescein pairs are preferred.

|  | Py-BiPy-tetraacid-Eu | TrisBiPy-Eu |
|---|---|---|
| Rhodamine6G | 20 Å | 22 Å |
| Tetramethylrhodamine | 38 Å | 43 Å |
| Sulforhodamine 101 | 45 Å | 55 Å |
| Merocyanine 540 | 31 Å | 41 Å |
| Atto565 | 36 Å | 45 Å |
| Cy3 | 26 Å | 24 Å |
| Atto550 | 26 Å | 34 Å |
| Cy3.5 | 48 Å | 41 Å |
| Dy547 | 25 Å < $R_0$ < 35 Å | — |
| Dy548 | 25 Å < $R_0$ < 35 Å | — |
| Dy549 | 25 Å < $R_0$ < 35 Å | — |
| Dy554 | 25 Å < $R_0$ < 35 Å | — |
| Dy555 | 25 Å < $R_0$ < 35 Å | — |
| Dy556 | 25 Å < $R_0$ < 35 Å | — |
| Dy560 | 25 Å < $R_0$ < 35 Å | — |
| mStrawberry | 44 A | 52 A |
| mCherry | 51 A | — |

The Alexa and oregon green compounds are sold by the company Invitrogen; the Atto compounds are sold by the company Attotec; the Dy compounds are sold by the company Dyomics; the Cy compounds are sold by the company Amersham Biosciences; the other compounds are sold by various suppliers of chemical reagents, such as the companies Sigma, Aldrich or Acros.

Among the above pairs, pairs of which the ROs are between 21 and 48 are preferred for the purposes of the invention.

By way of nonlimiting examples, the table hereinafter lists pairs of FRET partners of which the Förster radius is greater than 55 Å, and which therefore requires reading of the FRET signal with a delay of between 180 and 800 μs after excitation and an integration time of from 200 to 2000 μs.

|  | Tb(KR) | DTPA-cs124 Tb | Lumi4-Tb |
|---|---|---|---|
| Dy648 | 58 Å | 58 Å | 58 Å |
| Dy647 | 58 Å | 58 Å | 58 Å |
| Tetramethylrhodamine | 56 Å | 56 Å | 56 Å |
| Sulforhodamine 101 | 58 Å | 58 Å | 58 Å |
| Merocyanine 540 | 58 Å | 58 Å | 58 Å |
| Atto565 | 60 Å | 60 Å | 60 Å |
| Cy3 | 65 Å | 65 Å | 65 Å |
| Cy5 | 59 Å | 59 Å | 59 Å |
| Atto590 | 61 Å | 61 Å | 61 Å |
| Atto550 | 62 Å | 62 Å | 62 Å |
| Cy3.5 | 63 Å | 63 Å | 63 Å |
| Cy5.5 | 58 Å | 58 Å | 58 Å |
| Dy547 | >60 Å | >60 Å | >60 Å |
| Dy548 | >60 Å | >60 Å | >60 Å |
| Dy549 | >60 Å | >60 Å | >60 Å |
| Dy554 | >60 Å | >60 Å | >60 Å |
| Dy555 | >60 Å | >60 Å | >60 Å |
| Dy556 | >60 Å | >60 Å | >60 Å |
| Dy560 | >60 Å | >60 Å | >60 Å |
| Alexa647 | 58 Å | 58 Å | 58 Å |
| mCherry | 58 Å | — | 58 Å |
| mStrawberry | 60 Å | — | 60 Å |

|  | Py-BiPy-tetraacid-Eu | TrisBiPy-Eu |
|---|---|---|
| Alexa680 | 71 Å | 73 Å |
| Alexa700 | 76 Å | 81 Å |
| Alexa750 | 59 Å | 62 Å |
| Alexa647 | 65 Å | 65 Å |
| Cy5 | 66 Å | 64 Å |
| Cy5.5 | 71 Å | 72 Å |
| Cy7 | 59 Å | 64 Å |
| Dy647 | 65 Å | 65 Å |
| Dy648 | 65 Å | 65 Å |
| Atto590 | 59 Å | 62 Å |
| mCherry | — | 56 Å |

The Tb(KR)/Dy648, Lumi4-Tb/Dy648, Tb(KR)/Dy647 and Lumi4-Tb/Dy647 pairs are particularly preferred.

Labeling of Transmembrane Proteins with the Members of a Pair of FRET Partners

Another of the essential features of the invention lies in the fact that the labeling of transmembrane proteins comprising a VFT domain with an energy donor or energy acceptor is carried out in the N-terminal position of the VFT domains of each of the two subunits constituting the dimer.

Several techniques can be used to label the VFT-domain protein with a donor or an acceptor, in particular any of the techniques hereinafter may be used:

(a) Coupling of the VET-Domain Protein with a Donor or an Acceptor Indirectly (Noncovalently)

The donor or the acceptor can be coupled with the VFT-domain protein by means of a pair of binding partners of which at least one is of protein nature. In this approach, the VFT-domain protein is fused with the binding partner of protein nature by means of conventional molecular biology techniques (construction of an expression vector comprising a nucleotide sequence encoding the VFT-domain protein, fused with that encoding the protein binding partner, and introduction of the expression vector into the cell). According to the invention, the binding partner is present in the N-terminal portion of the VFT-domain protein, preferably at its end.

The donor or the acceptor is covalently conjugated to the other binding partner, which herein is referred to as coupling agent, that will subsequently be added to the extracellular medium. Recognition of the binding partners allows indirect labeling of the VFT-domain protein with the donor or the acceptor.

By way of nonlimiting examples of binding partners particularly suitable for implementing the invention, mention may be made of:

The pair consisting of the sequence cysteine-cysteine-X—X-cysteine-cysteine (SEQ ID No. 1), in which X is any amino acid, and of a biarsenic compound. These biarsenic compounds can be easily labeled with an organic molecule of the fluorescein or rhodamine type (see B. A. Griffin et al. (1998) Science. 1998, 281, 269-271 and S. A. Adams et al. (2002) J. Am. Chem. Soc. 2002, 124, 6063-6076 for details on the technology).

The BTX (bungarotoxin) peptide, composed of 13 amino acids, which is recognized by bungarotoxin (BTX), can be coupled to a fluorescent molecule (see C. M. McCann et al. (2005), Biotechnique (2005), 38, 945-952).

The streptavidin (or avidin)/biotin pair: the streptavidin binding sequence (SBP-Tag) is a sequence made up of 38 amino acids which has a high affinity for biotin that can be prelabeled with a donor or an acceptor (see C. M. McCann et al. (2005), Biotechnique (2005), 38, 945-952).

The sequence of the *E. coli* dihydrofolate reductase enzyme (eDHFR) which specifically and with high affinity binds ligands, such as trimethoprim, onto which the donor or the acceptor can be grafted according to the technique known as "Ligand link Universal labeling technology" from the company Active Motif.

Tag/antitag pairs are binding partners commonly used to label proteins. The term "tag" denotes a small protein "label" consisting of an amino acid sequence, which is generally but not necessarily quite short (less than 15 amino acids), and which is fused to the VFT-domain protein or else is naturally present in this protein. The term "antitag" denotes an antibody which binds specifically to said "tag". In this implementation, the "antitag" antibody is covalently bonded to the donor or to the acceptor. When the antibody thus labeled is added to the extracellular medium, it binds to the "tag" conjugated to the VFT-domain protein and the "tag/antitag" interaction allows indirect labeling of this protein with the donor or the acceptor.

By way of nonlimiting example of "tag/antitag" pairs, mention may be made of the following pairs, the members of which are commercially available: GST/anti-GST antibody in which GST represents glutathione S-transferase or a fragment thereof; 6HIS/anti-6HIS antibody in which 6HIS is a peptide consisting of six histidines; Myc/anti-Myc antibody in which Myc is a peptide consisting of amino acids 410-419 of the human Myc protein; FLAG/anti-FLAG antibody in which case FLAG is a peptide having the eight amino acids DYKD-DDDK (SEQ ID No. 2); HA/anti-HA antibody in which HA is an influenza hemagglutinin epitope consisting of the nine amino acids YPYDVPFYA (SEQ ID No. 3). It is clear that the exact nature of the tag is not essential for the implementation of the invention.

(b) Coupling of the VFT-Domain Protein with a Donor or an Acceptor Directly (Covalently)

In this approach, the donor or the acceptor is coupled to the VFT-domain protein by covalent bonding; several techniques have been described and the reagents necessary for the implementation thereof are commercially available. For this coupling, any of the techniques hereinafter may be used:

Formation of a covalent bond with a reactive group present on the VFT-domain protein, in particular with one of the following groups: the amino-terminal group, the carboxylate groups of aspartic and glutamic acids, the amine groups of lysines, the guanidine groups of arginines, the thiol groups of cysteines, the phenol groups of tyrosines, the indol rings of tryptophans, the thioether groups of methionines and the imidazole groups of histidines.

These groups present on the VFT-domain protein can form a covalent bond with a reactive group borne by the donor or the acceptor. Suitable reactive groups are known to those skilled in the art: a donor or an acceptor functionalized with a maleimide group will, for example, be capable of covalently bonding with the thiol groups borne by the cysteines of the protein. Likewise, a donor/acceptor bearing an N-hydroxysuccinimide ester will be capable of covalently bonding to an amine of the VFT-domain protein.

Use of a suicide enzyme

Suicide enzymes are proteins which have an enzymatic activity modified by specific mutations which give them the ability to rapidly and covalently bond a substrate. These enzymes are termed suicide enzymes because each one can bond just one fluorescent molecule, the activity of the enzyme being blocked by the binding of the substrate. These enzymes consequently constitute a tool of choice for specifically labeling proteins of interest with a ratio of one fluorescent molecule for one protein. By way of nonlimiting example, mention may be made of the following enzymes:

O6-alkylguanine DNA alkyltransferase (AGT) mutants. The Snap-tag (Juillerat et al., Chemistry & biology, Vol. 10, 313-317 April 2003) and Clip-tag (Gautier et al., Chemistry et Biology, 15, 128-136, February 2008) enzymes sold by the company NEB are mutants of human AGT of which the substrates are, respectively, O6-benzylguanine (hereinafter abbreviated to BG) and O2-benzylcytosine (hereinafter abbreviated to BC). The N-AGT enzyme (Gronemeyer et al., Protein engineering, design & selection, vol. 19, No. 7, pp 309-316, 2006) is another mutant of this enzyme, of which the reactivity with O6-benzylguanine is better than that of the Snap-tag enzyme. O6-alkylguanine DNA alkyltransferase mutants are the preferred suicide enzymes;

mutants of a dehalogenase (such as the HaloTag enzyme sold by Promega) which also generate an enzymatic reaction of the suicide type (see WO 04/072232 A2), some of the substrates of which are compounds of the chloroalkane family, in particular chloroalkanes comprising the —NH—$CH_2CH_2$—O—$CH_2CH_2$—O—$(CH_2)_6$—Cl motif. In this case, the donor/acceptor will be conjugated to this type of motif;

the ACP protein (acyl carrier protein), onto which the 4'-phosphopantethein residue of coenzyme A is transferred, in the presence of phosphopantethein transferase, on a serine of the ACP (N. George et al., Journal of the American Chemical society 126 (2004) p 8896-8897). When this approach is used to label the VFT-domain protein with the donor or the acceptor, it is necessary to add phosphopantethein transferase to the reaction medium. The company NEB sells an ACP fragment under the trade name "ACP-Tag" for labeling proteins.

In this approach, a suicide enzyme is fused with the VFT-domain protein in its N-terminal portion by conventional molecular biology techniques (production of an expression vector comprising the nucleic sequence encoding the suicide enzyme and that encoding the VFT-domain protein, and introduction of this vector into the cell), and the substrate of the enzyme, covalently bonded to a donor/acceptor, is introduced into the extracellular medium. The enzymatic reaction results in covalent bonding of the labeled substrate to the enzyme, and therefore labeling of the VFT-domain protein with the donor or the acceptor.

The use of suicide enzymes is particularly preferred for implementing the invention: in this case, the membrane protein comprising a VFT domain is expressed in the form of a fusion protein comprising the VFT-domain protein and, at its N-terminal end, a suicide enzyme or a suicide enzyme fragment capable of bonding covalently with its substrate: the labeling of the VFT-domain protein can then be carried out by addition, to the measuring medium, of one of the compounds that is a member of the pair of FRET partners, covalently bonded to the substrate of said suicide enzyme.

In one even more preferred implementation, each of the subunits constituting the dimer is expressed in the form of a fusion protein with a suicide enzyme. In this case, the suicide enzymes used for each subunit can be different or identical.

Maurel et al. have described the preparation of plasmids encoding a fusion protein comprising a suicide enzyme (Snap-tag) in the N-terminal portion of the VFT-domain protein (GABA B1, GABA B2, mGlu1) and the transfection of said plasmids into cells (Nature Methods, 2008, Supplementary methods). The methods used are general molecular biology techniques.

Measuring the FRET Signal

The FRET signal is measured conventionally using a fluorimeter which enables excitation of the measuring medium at the absorption wavelength of the energy donor and measurement of the luminescence emitted by the measuring medium at the emission wavelength of the donor compound and/or of the acceptor compound if the latter is fluorescent.

The luminescence emitted by the medium is detected after a delay following excitation, and for a period of time called the integration time, it being possible to adjust these two parameters on commercially available fluorimeters.

In one preferred embodiment, in particular when the Förster radius ($R_0$) of the pair of FRET partners is included in the range of 20 Å to 55 Å, the signal is measured with a delay of 20 to 100 µs after excitation, and an integration time of from 100 to 500 µs. The following time windows, individually, are preferred windows: 50-300 µs, 50-400 µs, 50-450 µs, 40-250 µs, 100-300 µs.

In another preferred embodiment, and regardless of the Förster radius ($R_0$) of the pair of FRET partners, the signal is measured with a delay between 180 and 800 µs after excitation and an integration time of from 200 to 2000 µs. The following time windows, individually, are preferred windows: 300-650 µs, 500-1000 µs, 500-1500 µs, 800-1800µs. As mentioned above, the latter embodiment is obligatory when the Förster radius ($R_0$) of the pair of FRET partners is greater than 55 Å.

The energy donor and acceptor compounds coming closer together causes an increase in energy transfer (increase in FRET) which will result in:
 an increase in the luminescence emitted at the emission wavelength of the acceptor if it is fluorescent;
 a decrease in the luminescence emitted at the emission wavelength of the donor; a decrease in the lifetime of fluorescence of the donor compound.

The change in the FRET signal can therefore be measured by detecting the luminescence emitted by the donor or that emitted by the acceptor. Preferably, the FRET signal is measured by detecting the luminescence emitted by the acceptor compound.

Even more preferably, the FRET variations are measured by detecting both (but not necessarily simultaneously) the luminescence emitted by the donor compound at its emission wavelength and the luminescence emitted by the acceptor at its emission wavelength, then by correcting the signal obtained for the acceptor with that obtained for the donor, for example by calculating the ratio of the two values. In this case, an "increase in FRET" will correspond to an increase in the acceptor/donor ratio. Fluorimeters generally include a mode that allows this type of reading. Moreover, the luminescence of the donor and acceptor compounds is not necessarily measured in the same time window.

It is particularly advantageous to carry out the FRET measurements as time-resolved FRET (TR-FRET), which is possible with energy donor compounds having a long lifetime, since this type of measurement makes it possible to eliminate a large number of interferences. Even though the method according to the invention can be implemented in the FRET mode, the TR-FRET mode is greatly preferred.

Reagent Kits

The invention also relates to kits of components for implementing the method according to the invention, i.e. comprising the reagents described above, optionally accompanied by instructions for their use according to the invention. In particular, such kits comprise:
- cell membranes comprising dimers of VFT-domain proteins, said dimers consisting of a first protein and of a second protein, said proteins being identical or different, a pair of FRET partners,
- means for labeling the N-terminal portion of the VFT domain of said first protein with a member of said pair of FRET partners and means for labeling the N-terminal portion of the VFT domain of said second protein with the other member of said pair of FRET partners,
- instructions according to which the FRET signal must be measured within a time window in which the signals measured in the presence and in the absence of a reference agonist or antagonist compound are different.

The latter instructions may consist of the mention of an appropriate time window, as indicated above for the method according to the invention.

In one particular embodiment, these kits comprise:
(i) either a pair of FRET partners of which the Förster radius ($R_0$) is between 20 and 55 Å, and instructions according to which the FRET signal must be measured with a delay of between 20 and 100 μs after excitation and an integration time of from 100 to 500 μs;
(ii) or a pair of FRET partners of which the Förster radius ($R_0$) is greater than 55 Å, and instructions according to which the FRET signal must be measured with a delay of between 180 and 800 μs after excitation and an integration time of from 200 to 2000 μs.

In one particularly preferred embodiment, the labeling means consist of the use of suicide enzymes for covalently labeling the constituent proteins of the dimer. In this embodiment, said first and second proteins are each expressed in the form of a fusion protein with a suicide enzyme, and the members of the pair of FRET partners are each covalently bonded to the substrate of said suicide enzyme.

It is possible for the components of the kits according to the invention to form just one product, for example if said first and second constituent proteins of the dimer studied are each labeled with a member of said pair of FRET partners. Thus, the invention also relates to kits containing cell membranes comprising dimers of VFT-domain proteins, said dimers consisting of a first protein and of a second protein, said proteins being identical or different, each of these proteins being labeled, in the N-terminal portion of its VFT domain, with a member of a pair of FRET partners, said kit also comprising instructions according to which the FRET signal is detected within a time window in which the signals measured in the presence or in the absence of a reference agonist or antagonist compound are different.

EXAMPLES

The following products are used in examples 1 to 12:

Reagents:

Modulators (Agonists, Antagonists, Allosteric Modulators):

DCG IV, L-glutamic acid and LY341495 are available in the Tocris Biosciences catalog. The 4-MPPTS (positive allosteric modulator of the mGluR2 receptor, also called LY487379) was donated by Addex Pharmaceuticals, its synthesis is described in U.S. Pat. No. 6,800,651.

Culture Media:

DMEM, DMEM+Glutamax, MEM-NEAA, MEM-Penicillin/Streptomycin, Trypsin/EDTA are available in the Gibco catalog. The fetal calf serum used is of the Lonza brand, South American type (batch 7SB0017).

Fluorescent Conjugates:

BG-Lumi4-Tb: benzylguanine-Lumi4-Tb conjugate, sold by Cisbio Bioassays (Tag-lite® SNAP-Lumi4Tb). BG is the substrate of the Snap-tag enzyme.

BC-fluorescein: benzylcytosine-fluorescein conjugate, sold by the company NEB under the trade name CLIP-Vista Green. BC is the substrate of the Clip-tag enzyme.

BG-fluorescein: benzylguanine-fluorescein conjugate, sold by the company NEB under the trade name SNAP-Vista Green (New England Biolabs).

Tag-lite® SNAP-Green: benzylguanine-fluorescein conjugate, sold by the company Cisbio Bioassays.

Tag-lite® SNAP-red: benzylguanine-cyanine derivative conjugate of which the emission peak is at 670 nm, sold by Cisbio Bioassays.

Other Reagents:

DMSO, Tris (Trizma Base), NaCl, $KH_2PO_4$, $MgSO_4$, KCl and $CaCl_2$ are available in the Sigma-Aldrich catalog.

Plasmids Used for Expression of the GPCR1-GPCR2 Dimers:

Expression vectors comprising the DNA encoding the HA-Snaptag-[GPCR1] and Flag-Cliptag-[GPCR2] fusion proteins, in which GPCR1 and GPCR2 represent the GPCRs that are intended to be expressed by the cell, were prepared from the prK5 vector by conventional molecular biology techniques, and their sequences were verified by sequencing. Its sequence, which contains 4661 base pairs, is the sequence SEQ ID No. 4. The positions of the unique restriction sites in this plasmid are indicated hereinafter:

| | |
|---|---|
| SpeI | 28 |
| NdeI | 263 |
| SacII | 684 |
| EagI | 684 |
| ClaI | 913 |
| EcoRI | 919 |
| SmaI | 927 |
| BamHI | 930 |
| XbaI | 936 |
| SalI | 942 |

| | |
|---|---|
| PstI | 952 |
| HindIII | 954 |
| KpnI | 1173 |
| StuI | 1518 |
| HpaI | 1542 |
| NarI | 1710 |

The vectors, hereinafter referred to as prK5-HA-Snaptag-[GPCR1] or prK5-Flag-Cliptag-[GPCR2], contain a CMV promoter, an ATG start codon, the DNA sequence encoding the signal peptide of mGluR5, an influenza hemagglutinin epitope (HA) or the FLAG epitope, the DNA sequence encoding the Snap-tag enzyme or that of the Clip-tag enzyme, the DNA sequence encoding the [GPCR1] or [GPCR2] receptor with the exception of their start codons and of the sequences encoding their signal peptide, if it exists, and, finally, a stop codon.

The sequences of the plasmids encoding the HA-Snaptag-$mGluR_2$ and Flag-Cliptag-$mGluR_2$ fusion proteins used in example 1 are the sequences SEQ ID No. 5 and SEQ ID No. 6.

In the sequence SEQ ID No. 5, the position of the coding regions is respectively:
signal peptide of $mGluR_5$: 937-1002;
HA epitope: 1009-1035;
Snap-tag: 1042-1590;
$mGluR_2$: 1597-4149.

In the sequence SEQ ID No. 6, the position of the coding regions is respectively:
signal peptide of $mGluR_5$: 937-1002;
FLAG: 1015-1038;
Clip-tag: 1045-1593;
$mGluR_2$: 1600-4152.

The plasmids comprising the sequences of other receptors are identical with the exception of the region encoding the receptor of interest. The sequences of the various receptors used are accessible in the Genbank data bank.

Those skilled in the art will be able to readily construct these plasmids either by subcloning from plasmids already described in the literature (Maurel et al., mentioned above), or directly by gene synthesis.

Cells: The Cos-7 cell line, which is commercially available, was used.

Complete medium: DMEM+10% fetal calf serum+MEM-NEAA+MEM-penicillin/streptomycin.

Electroporation buffer: 50 mM $KH_2PO_4$, 20 mM $CH_3COOK$, 20 mM KOH, 50 mM $MgSO_4$.

Labeling buffer: DMEM+glutamax.

Washing and reading buffer: 20 mM Tris, 118 mM NaCl, 1.2 mM $KH_2PO_4$, 1.2 mM $MgSO_4$, 4.7 mM KCl, 1.8 mM $CaCl_2$; pH adjusted to 7.4.

Example 1

Demonstration of an Activating Compound having an Agonist Effect on an $mGluR_2$-$mGluR_2$ Dimer ($R_0$ of the Pair of FRET Partners Used: 48 Å) Protocol Transfection by Electroporation:

Cos-7 cells were cultured in complete medium at 37° C. and 5% $CO_2$. At confluence, they were washed once with PBS, and detached with a trypsin-EDTA solution for 10 min at 37° C. A suspension of 10 million cells was mixed with 5 µg of total DNA (3.5 µg of prK5 plasmid, 1.2 µg of prK5Flag-Cliptag-mGluR2 plasmid and 0.3 µg of prK5HA-Snaptag-mGluR2 plasmid), in a final volume of 300 µl of electroporation buffer, and were then subjected to an electric shock of 280 V, 900 µF using a Gene-Pulser II electroporator (BIO-RAD), in 4 mm electroporation cuvettes (Eurogentec). The cells were then seeded into a 96-well plate (Greiner CellStar 96-well plate), at 150 000 cells per well, in a final volume of 100 µl per well of complete medium, and then incubated for 24 hours.

Labeling 24 hours after transfection, the cells were incubated for 2 h at 37° C. in the presence of 50 µl of labeling buffer +0.3 µM BG-Lumi4-Tb and 1 µM BC-fluorescein.

The cells were then washed four times with 100 µl of washing buffer, and the reading was carried out in 100 µl of washing buffer.

Reading

The fluorescence emitted at the wavelength of fluorescein (acceptor) was read on an Analyst AD microplate reader (Molecular Devices) in TRF mode, delay 50 µs, integration time 450 µs, excitation filter 320 nm bandwidth (BW) 25, BB/UV dichroic mirror, emission filters 520 nm BP10. This FRET signal is hereinafter denoted TRF520. The plate was read a first time in the absence of glutamate.

20 µl of glutamate solution were then added to the 100 µl of reading buffer, so as to obtain final concentrations in the well (total volume of 120 µl) of 316 µM; 100 µM; 31.6 µM; 10 µM; 3.16 µM; 1 µM; or 0.316 µM.

After addition of the glutamate, the plate was read a second time.

Results

Figure 1:
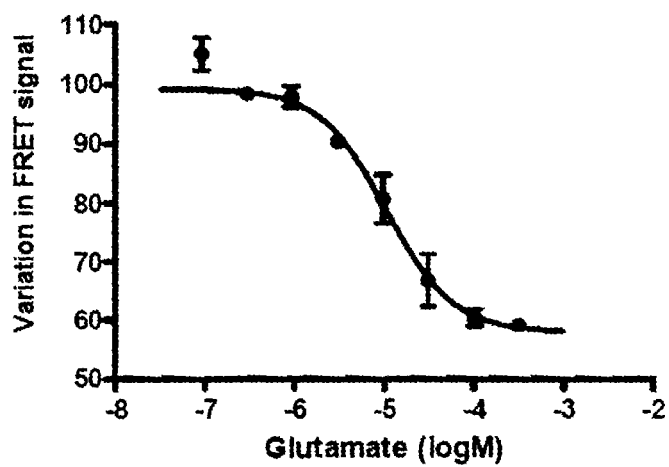
FIG. 1 represents the variation in FRET signal emitted by an mGluR2-mGluR2 dimer as a function of glutamate concentration.

FIG. 1 represents the TRF520 signal as a function of glutamate concentration. This signal is expressed as percentage of TRF520 read at the first reading, i.e. before addition of the glutamate, i.e.:

$$TRF520(\%) = \frac{TRF520 \text{ signal read after addition of glutamate}}{TRF520 \text{ signal read before addition of glutamate}} \times 100$$

In the presence of agonist (glutamate), a decrease in TRF520 is observed, and can be attributed neither to a decrease in the fluorescence of the cryptate, nor to a decrease in the fluorescence of the acceptor. This indicates that there was a variation in efficiency of energy transfer (FRET) between the donor and acceptor compounds, which may in particular be due to a variation in distance between the fluorophores.

This variation is dose-dependent, i.e. it depends on the concentration of the glutamate agonist. The curve is in the shape of a sigmoid curve; the concentration necessary to have a variation in TRF520 equal to half the maximum variation corresponds very closely to the pharmacological $EC_{50}$ of glutamate on the mGlu2 receptor. This strongly suggests that the phenomenon observed during the variation in TRF520 is the activation of the receptor.

This example shows that the method according to the invention makes it possible to demonstrate dimer-activating compounds, in particular agonist compounds. In the case of the $mGluR_2$ homodimer, the activating compounds cause a reduction in TRF520 signal.

Example 2

Demonstration of a Deactivating Compound having a Competitive Antagonist Effect on an mGluR2-mGluR2 Dimer ($R_0$ of the Pair of FRET Partners Used: 48 Å)

Reagents and Plasmids

The same reagents and plasmids as those described in example 1 were used. The known antagonist compound LY341495 (Tocris Bioscience) was used.

Protocol

The same protocol as that described in example 1 was used. The final concentrations were [Glutamate]=100 µM in all the wells and [LY341495]=1000 nM; 316 nM; 100 nM; 31.6 nM; 10 nM; 3.16 nM; or 1 nM.

Results

Figure 2:
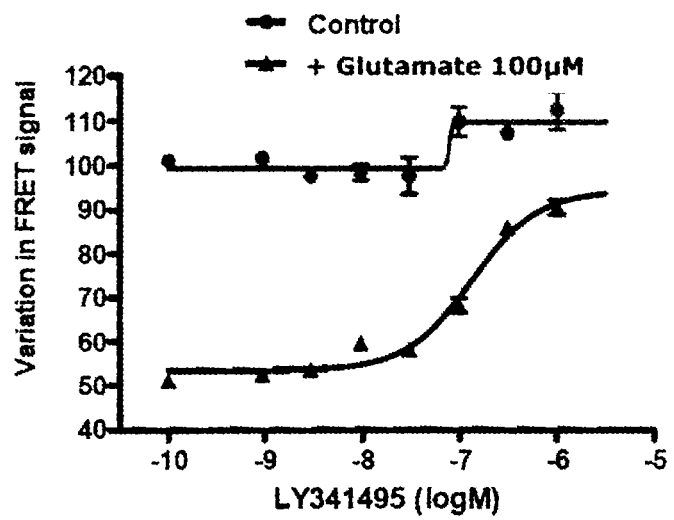
FIG. 2 represents the variation in FRET signal emitted by an mGluR2-mGluR2 dimer as a function of the concentration of LY341495 antagonist and in the presence or absence of glutamate.

FIG. 2 represents the TRF520 signal as a function of the concentration of LY341495 antagonist and in the presence of a constant concentration of glutamate (control curve: in the absence of glutamate).

In the presence of glutamate and in the absence of the competitive antagonist LY341495, the receptor is activated, and a variation in TRF520 of 50% is observed. The presence of antagonist prevents this action of glutamate on the TRF520, and the signal measured in the presence of increasing concentrations of antagonist increases, as opposed to what is observed in the presence of increasing concentrations of agonist (example 1). When the concentration of antagonist is at a maximum (1 µM), the variation in FRET induced by the agonist is completely inhibited (100%). The concentration necessary to inhibit 50% of the variation in FRET induced by glutamate, in this case 150 nM, is not very different than the concentration necessary to inhibit 50% of the pharmacological action of glutamate ($IC_{50}$).

This example shows the effectiveness of the method according to the invention for demonstrating the deactivating effect of a known antagonist compound. By proceeding in a similar manner with a test compound, it is possible to determine whether this compound has an antagonist effect.

Example 3

Demonstration of an Activating Compound having a Partial Agonist Effect on an mGluR2-mGluR2 Dimer ($R_0$ of the Pair of FRET Partners Used: 48 Å)

Reagents and Plasmids

The same reagents and plasmids as those described in example 1 were used. The known partial agonist compound used was DCG-IV (Tocris Bioscience); it was compared with the reference complete agonist, glutamate.

Protocol

The protocol of example 1 was used. The final concentrations of [DCG-IV] were the following: 100 µM; 31.6 µM; 10 µM; 3.16 µM; 1 µM; 0.316 µM; or 0.1 µM.

Results

Figure 3:
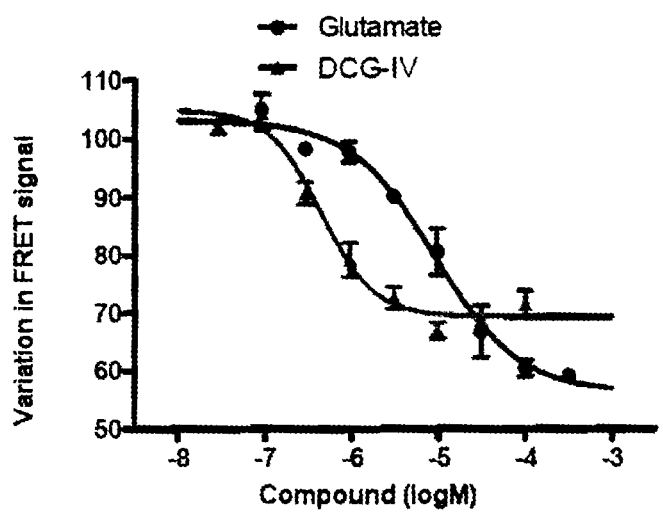
FIG. 3 represents the variation in FRET signal emitted by an mGluR2-mGluR2 dimer as a function of the concentration of glutamate or of DCG-IV (partial agonist).

FIG. 3 represents the TRF520 signal as a function of the concentration of glutamate (complete agonist) or of DCG-IV (partial agonist).

Like glutamate, DCG-IV is capable of inhibiting the TRF520 signal in a dose-dependent manner. The concentration necessary for obtaining a variation equal to half the maximum variation is close to the pharmacological $EC_{50}$ of DCG-IV (0.4 µM). Nevertheless, the maximum variation obtained with DCG-IV is 30%, whereas it is 50% with glutamate. This result confirms the partial agonist nature of DCG-IV, which causes a maximum variation in FRET that is less than that obtained with the reference agonist. This example shows that the method according to the invention can be used for selecting compounds having an activating effect of partial agonist type on mGluR$_2$ dimers.

Example 4

Demonstration of an Activating Compound having a Positive Allosteric Modulator (PAM) Effect on an mGluR2-mGluR2 Dimer ($R_0$ of the Pair of FRET Partners Used: 48 Å)

Reagents and Plasmids

The reagents and plasmids of example 1 were used. A known positive allosteric modulator compound was used, 4-MPPTS (=the mGluR2 PAM, also called LY487379).

Protocol

The protocol described in example 1 was used.

The final concentrations were [4-MPPTS]=10 µM and [glutamate]=1000 µM; 316 µM; 100 µM; 31.6 µM; 10 µM; 3.16 µM or 1 µM.

Results

Figure 4:
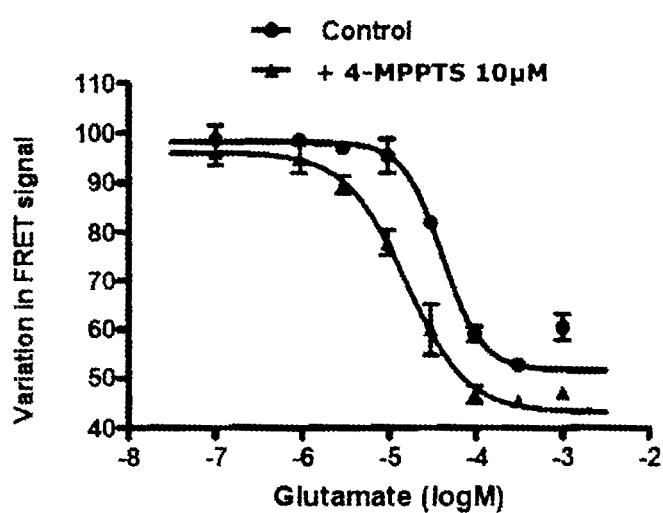
FIG. 4 represents the variation in FRET signal emitted by an mGluR2-mGluR2 dimer as a function of glutamate concentration in the presence or absence of 4-MPPTS (positive allosteric modulator).

FIG. 4 represents the change in TRF520 signal as a function of glutamate concentration in the presence or in the absence (control) of 4-MPPTS.

For a given glutamate concentration, a greater decrease in signal is observed in the presence of 4-MPPTS than in its absence.

This example shows that the method according to the invention can be used to demonstrate compounds having a positive allosteric modulating effect.

Example 5

Labeling with Two Different Suicide Enzymes is Not Required ($R_0$ of the Pair of FRET Partners Used: 48 Å)

In this example, a single plasmid, prK5-HA-Snaptag-mGluR2, was used to express the mGluR2 homodimers. The protocol is the same as that used in example 3, the only difference being that the amounts of transfected DNA are: 4 µg of prK5+1 µg of prK5-HA-Snaptag-mGluR2.

The following fluorescent conjugates were used: BG-Lumi4-Tb at a concentration of 0.1 µM in the labeling medium, and BG-fluorescein at 0.02 µM.

Figure 5:
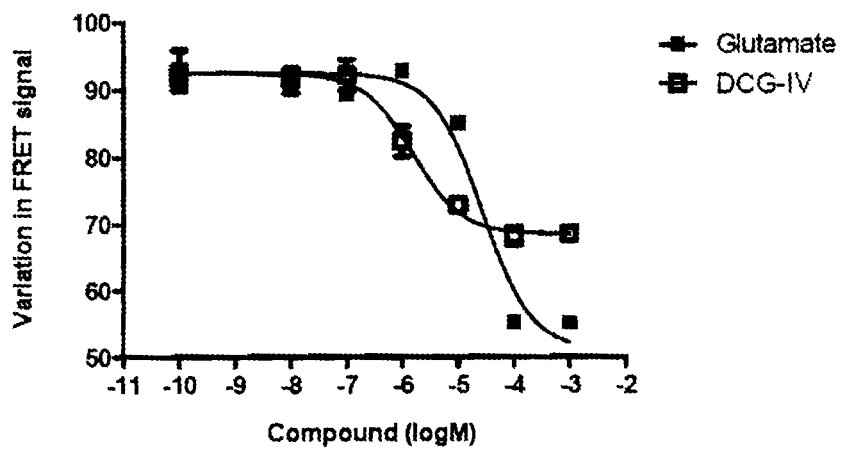
FIG. 5 represents the variation in FRET signal emitted by an mGluR2-mGluR2 dimer (Snap-tag labeling on each subunit) as a function of the concentration of glutamate or of DGC-IV.

FIG. 5 shows the change in FRET signal as a function of increasing concentrations of glutamate and of DGC-IV, and shows that each of the proteins forming the dimer, in this case each of the mGluR2s forming the homodimer, can be labeled in the same way, in this case via a BG/Snap-tag approach. The use of two different suicide enzymes is not therefore essential.

Example 6

Demonstration of an Activating Compound having an Agonist Effect on the mGluR2-mGluR2, mGluR3-mGluR3 or mGluR4-mGluR4 Homodimers ($R_0$ of the Pair of FRET Partners Used: 48 Å)

Example 1 was reproduced with plasmids enabling the expression either of mGluR3-mGluR3 homodimers or of mGluR4-mGluR4 homodimers. The procedure for obtaining the prK5-HA-Snaptag-mGlu3, prK5-Flag-Cliptag-mGlu3, prK5-HA-Snaptag-mGlu4 and prK5-Flag-Cliptag-mGlu4 plasmids is described in the "plasmids used" section. The protocol described in example 1 was followed, the only difference being that the amounts of DNA transfected are:
for mGlu2: identical to example 1;
for mGlu3: 3.5 µg of prK5 plasmid, 1.2 µg of prK5 Flag-Cliptag-mGluR3 plasmid and 0.3 µs of prK5 HA-Snaptag-mGluR3 plasmid;
for mGlu4: 3.5 µg of prK5 plasmid, 1.2 µg of prK5 Flag-Cliptag-mGluR4 plasmid and 0.3 µg of prK5 HA-Snaptag-mGluR4 plasmid.

Figure 6:
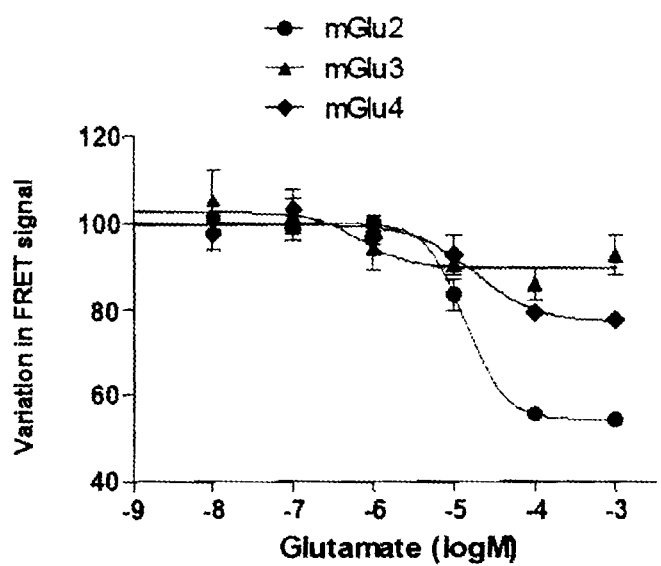
FIG. 6 represents the variation in FRET signal emitted by the mGluR2-mGluR2, mGluR3-mGluR3 and mGluR4-mGluR4 dimers, as a function of glutamate concentration.

The dose-response curves obtained are represented in FIG. 6. The results obtained in example 1 with the mGluR2-mGluR2 homodimer are confirmed with mGluR4-mGluR4 and mGluR3-mGluR3, even though the variation in signal observed on the latter receptor is not as great as that measured in the other cases.

This example shows that the method according to the invention can be implemented with the various metabotropic glutamate receptors.

Example 7

The Case of the mGlu3 Sensor

Antagonist-Sensitive, Not Very Agonist-Sensitive ($R_0$ of the Pair of FRET Partners Used: 48 Å)

Figure 7:
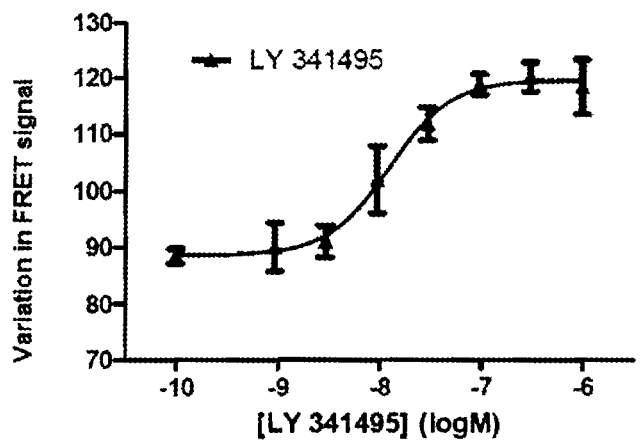
FIG. 7 represents the variation in FRET signal emitted by an mGluR3-mGluR3 dimer as a function of LY341495 concentration.

In this example, the protocol of example 1 was used with the plasmids and the amounts hereinafter:
3.5 µg of prK5 plasmid, 1.2 µg of prK5 Flag-Cliptag-mGluR3 plasmid and 0.3 µg of prK5-HA-Snaptag-mGluR3 plasmid were used in order to obtain the expression of the labeled mGluR3 homodimer.
Increasing concentrations of the LY 341495 antagonist were used to obtain the final concentrations: 1 µM, 320 nM, 100 nM, 32 nM, 10 nM, 3.2 nM and 1 nM.
Results
FIG. 7 represents the TRF520 signal as a function of the LY341495 concentration.
The addition of the antagonist causes an increase in the TRF520 signal, in a dose-dependent manner.
This example shows that the method according to the invention can be implemented in order to screen for molecules that deactivate the receptor of interest.

Example 8

Demonstration of an Activating Compound having an Agonist Effect on the mGluR2-mGluR2, mGluR3-mGluR3 or mGluR4-mGluR4 Homodimers and the mGluR2-mGluR3 and mGluR2-mGluR4 Heterodimers ($R_0$ of the Pair of FRET Partners Used: 48 Å)

Figure 8:
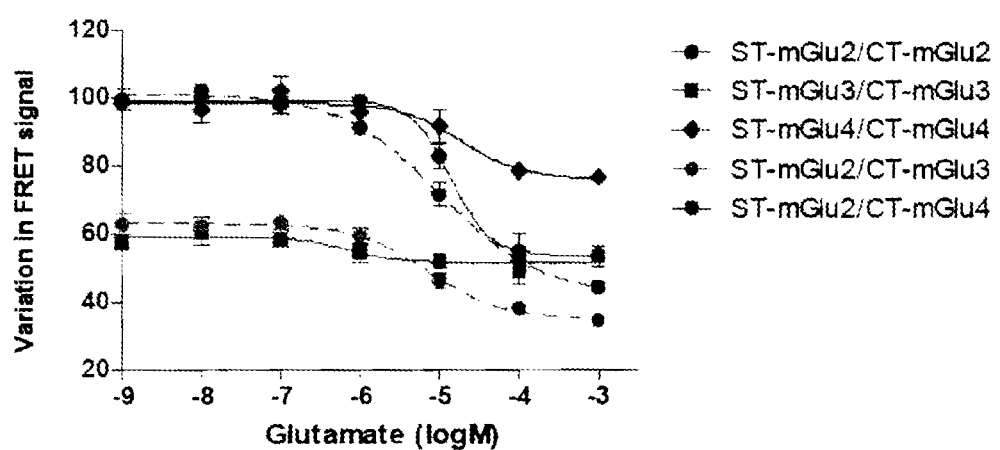
FIG. 8 represents the variation in FRET signal emitted by the mGluR2-mGluR2, mGluR3-mGluR3, mGluR4-mGluR4, mGluR2-mGluR3 and mGluR2-mGluR4 dimers as a function of glutamate concentration.

Example 1 was reproduced with the plasmids enabling the expression of mGluR2-mGluR2, mGluR3-mGluR3 or mGluR4-mGluR4 homodimers or of mGluR2-mGluR3 and mGluR2-mGluR4 heterodimers. The dose-response curves obtained are represented in FIG. 8. The results obtained in examples 1 and 6 are confirmed.

This example shows that the method according to the invention can be implemented not only with homodimers, but also with inter-subtype heterodimers of metabotropic glutamate receptors.

Example 9

Demonstration of the Effect of a Modulating Compound on the mGluR1-mGluR1 and mGluR8-mGluR8 Homodimers ($R_0$ of the Pair of FRET Partners Used: 48 Å)

Cells expressing the mGluR1-mGluR1, mGluR2-mGluR2, mGluR3-mGluR3 and mGluR8-mGluR8 homodimers were prepared according to an approach similar to that described in example 5, each mGluR receptor being expressed in the form of a fusion protein with the Snap-tag enzyme.

The labeling was carried out with the fluorescent conjugates hereinafter: BG-Lumi4-Tb (donor) at a concentration of 0.1 µM in the labeling medium and BG-fluorescein (acceptor) at 0.1 µM.

The fluorescence emitted at the wavelength of fluorescein (520 nm) and the fluorescence emitted at the wavelength of terbium (620 nm) were measured on an Infinit 500 microplate reader with a delay of 50 µs and an integration time of 400 µs.

These measurements were carried out in the presence of labeling buffer, or else of agonist (1 mM glutamate) or antagonist (0.1 mM LY341495).

The ratio of the signals emitted at 520 nm and 620 nm was calculated, and is hereinafter referred to as the "FRET ratio".

FIG. 9 represents the variation in FRET ratio observed in the presence of agonist (glutamate) or of antagonist (LY341495), or in the absence of these compounds to (buffer). The 100% value is selected arbitrarily as that observed in the presence of antagonist.

These results confirm those obtained in the previous examples for the mGluR2 and mGluR3 homodimers, and also show that the method according to the invention makes it possible to observe a variation in FRET signal when the mGluR8 and mGluR1 homodimers are brought into contact with agonists or antagonists.

Example 10

Demonstration of the Effect of a Modulating Compound on the mGluR1, mGluR2, mGluR3, mGluR4, mGluR5 and mGluR8 Homodimers ($R_0$ of the Pair of FRET Partners Used: 48 Å)

Example 9 was reproduced with the mGluR1, mGluR2, mGluR3, mGluR4, mGluR5 and mGluR8 homodimers, and the fluorescence was this time measured with a delay of 500 µs and an integration time of 1000 µs.

The results of FIG. 10 confirm those observed previously, namely that the method according to the invention is suitable for demonstrating compounds that modulate most of the mGluR receptors.

Example 11

Demonstration of the Effect of a Modulating Compound on the mGluR8 Homodimers ($R_0$ of the Pair of FRET Partners Used: 58 Å)

Example 9 was reproduced with a cell expressing the mGluR8-mGluR8 dimer, but the fluorescent compounds used have an R0>55 Å. In this case, the labeling was carried out with BG-Lumi4Tb (donor, 0.1 µM) and Tag-lite® SNAP-red (acceptor, 0.25 µM).

Figure 11:
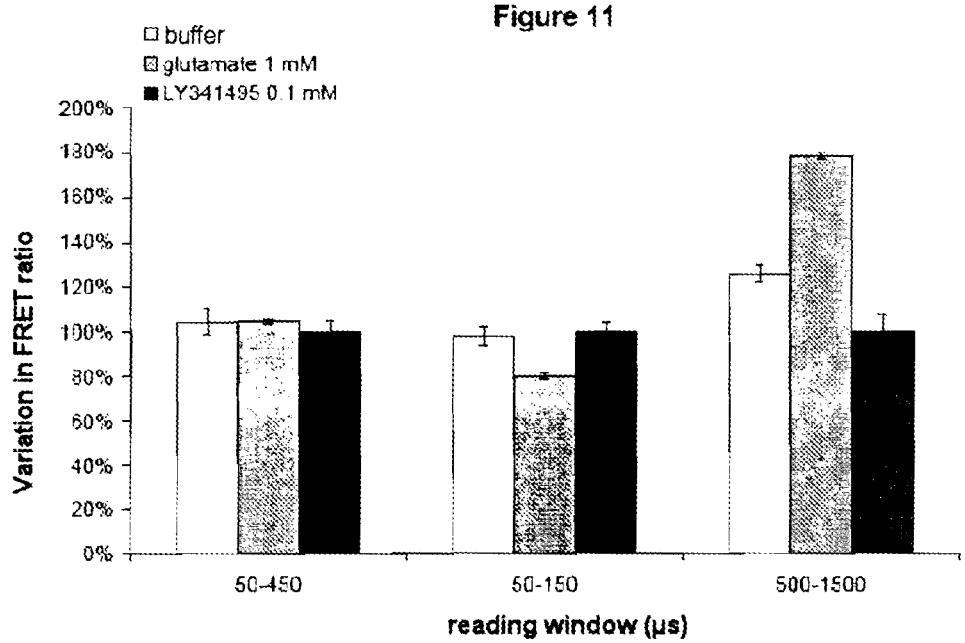
FIG. 11 represents the variation in the ratio of FRET emitted by an mGluR8-mGluR8 dimer, as a function of the time window, in the presence of glutamate or of LY341495, or in the absence of these compounds.

The fluorescence was measured on a Rubystar reader at 665 nm (acceptor) and 620 nm (donor) within the following time windows: 50-450 µs, 50-150 µs and 500-1500 µs (FIG. 11).

No significant variation in signal is observed in the presence of modulating (agonist or antagonist) compound when the signal is measured within the window conventionally used, namely 50-450 µs. A significant variation in the presence of agonist is observed when the fluorescence is measured within the 50-150 µs time window. Very significant variations in the presence of agonist or of antagonist are observed when the fluorescence is measured within the 500-1500 µs time window.

Example 12

Demonstration of the Effect of a Modulating Compound on the mGluR8 and mGluR2 Homodimers with a Pair of FRET Partners of which R0>55 Å: BG-TrisBiPy-pentaacid-Eu and Tag-lite® SNAP-Red ($R_0$ of the Pair of FRET Partners Used: 58 Å)

Example 9 was reproduced with cells expressing the mGluR8-mGluR8 dimer or the mGluR2-mGluR2 dimer, but the fluorescent compounds used have an R0>55 Å. In this case, the labeling was carried out with a europium cryptate coupled to benzylguanine (BG-TrisBiPy-pentaacid-Eu, donor, 0.2 µM) and Tag-lite® SNAP-red (acceptor, 0.25 µM).

Figure 12:
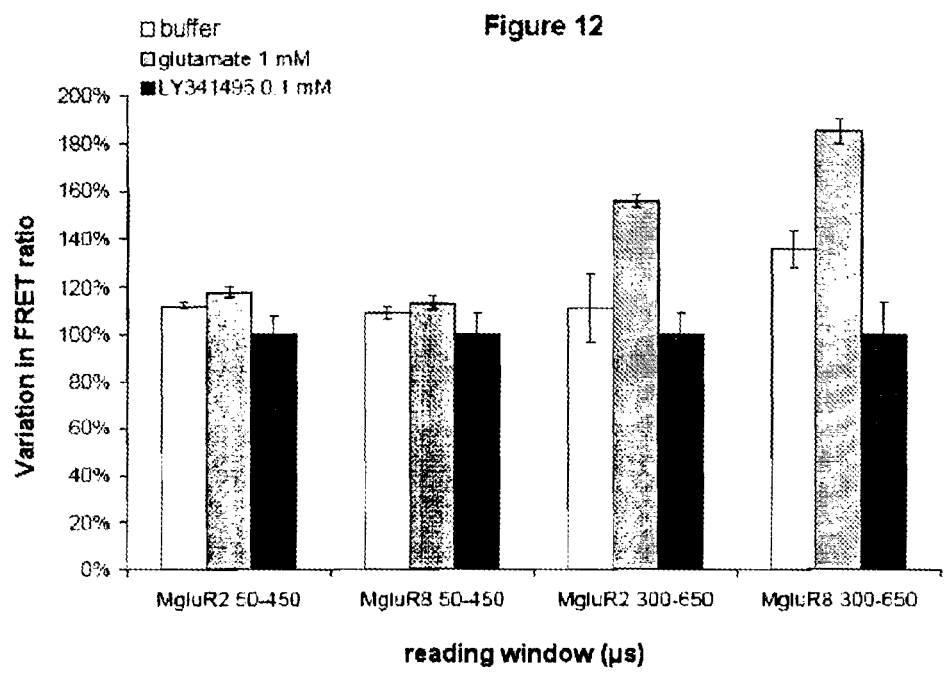
FIG. 12 represents the variation in the ratio of FRET emitted by the mGluR8-mGluR8 and mGluR2-mGluR2 dimers, as a function of the time window, in the presence of glutamate or of LY341495, or in the absence of these compounds.

The fluorescence was measured on a Rubystar reader at 665 (acceptor) and 620 (donor) within the following time windows: 50-450 µs and 300-650 µs (FIG. 12).

No significant variation in signal is observed in the presence of modulating (agonist or antagonist) compound when the signal is measured within the window conventionally used, namely 50-450 µs. Significant variations in the presence of agonist or of antagonist are observed when the fluorescence is measured within the 300-650 µs time window.

---

The invention claimed is:

1. A method for selecting compounds having a modulating effect on the activation state of a dimer of VFT-domain proteins expressed in cell membranes present in a measuring medium, said dimer consisting of a first protein and a second protein, each of the first protein and the second protein having a VFT domain, said proteins being identical or different, wherein the method comprises the following steps:
   (a) labeling the first protein in the N-terminal portion of the VFT domain thereof with a member of a pair of FRET partners;
   (b) labeling the second protein in the N-terminal portion of the VFT domain thereof with the other member of said pair of FRET partners;
   (c) exciting the FRET partners and measuring a FRET signal in the absence and in the presence of a test compound:
   (d) selecting the test compound as a modulating compound if a difference in the FRET signal in the absence and in the presence of the test compound is measured in step (c),
   wherein the FRET signal measured in step (c) is within a time window in which the signals measured in the presence and in the absence of a reference agonist or antagonist compound are different.

2. The method as claimed in claim 1, wherein the signal measured in step (c) is done so with a delay of between 180 and 800 µs after excitation and an integration time of from 200 to 1000 µs.

3. The method as claimed in claim 1, wherein:
   (i) a Förster radius ($R_0$) of said pair of FRET partners is between 18 and 55 Å, and the signal measured in step (c) is done so with a delay of between 20 and 100 µs after excitation and an integration time of from 100 to 500 µs; or
   (ii) Förster radius ($R_0$) of said pair is greater than 55 Å, and the signal measured in step (c) is done so with a delay of between 180 and 800 µs after excitation and an integration time of from 200 to 1000 µs.

4. The method as claimed in claim 1, wherein the FRET measurements in the presence and the absence of test compound are carried out in the presence of a known agonist of said dimer.

5. The method as claimed in claim 1, wherein said first and second proteins are class C G-protein coupled receptors comprising a VFT domain.

6. The method as claimed in claim 1, wherein said dimer of VFT-domain proteins is selected from: a metabotropic glutamate receptor, a gamma-aminobutyric acid receptor, a receptor linked to sweet taste perception, a receptor linked to umami taste perception, an extracellular calcium-sensing receptor and a basic amino acid receptor.

7. The method as claimed in claim 1, wherein the dimer of VFT-domain proteins is a metabotropic glutamate receptor, or is selected from TAS1R2-TAS1R3 and TAS1R1-TAS1R3.

8. The method as claimed in claim 1, wherein the labeling of the first and the second proteins with the members of a pair of FRET partners is either indirect labeling by means of a pair of binding partners, or direct labeling by covalent bonding.

9. The method as claimed in claim 8, wherein each of said first and second proteins is expressed in a form of a fusion protein with a suicide enzyme, and wherein the labeling of the first and of the second proteins is carried out by adding, to the measuring medium, the members of said pair of FRET partners, each one being covalently bonded to the substrate of said suicide enzyme.

10. The method as claimed in claim 9, wherein the first and second proteins are each expressed in the form of a fusion protein with a different suicide enzyme.

11. The method as claimed in claim 10, wherein the suicide enzyme is selected from an O6-alkylguanine DNA alkyltransferase mutant, a dehalogenase mutant, and a fragment of the acyl carrier protein.

12. The method as claimed in claim 9, wherein the first and second proteins are each expressed in the form of a fusion protein with the same suicide enzyme.

13. The method as claimed in claim 12, wherein the suicide enzyme is selected from an O6-alkylguanine DNA alkyltransferase mutant, a dehalogenase mutant, and a fragment of the acyl carrier protein.

14. The method as claimed in claim 9, wherein the suicide enzyme is selected from: an O6-alkylguanine DNA alkyltransferase mutant, a dehalogenase mutant, and a fragment of the acyl carrier protein.

15. The method as claimed in claim 1, wherein said pair of FRET partners consists of:
   (i) a fluorescent donor compound selected from: a europium chelate, a terbium chelate, a europium cryptate and a terbium cryptate and
   (ii) an acceptor fluorescent compound which is a fluorescent organic molecule selected from: rhodamines, cyanins, squaraines, coumarins, proflavins, acridines, fluoresceins, nitrobenzoxadiazole, cyan fluorescent proteins, green fluorescent proteins, yellow fluorescent proteins, orange and red fluorescent proteins, and proteins that are fluorescent in the far-red range.

* * * * *

SEQUENCE LISTING

```
<160> NUMBER OF SEQ ID NOS: 9

<210> SEQ ID NO 1
<211> LENGTH: 6
<212> TYPE: PRT
<213> ORGANISM: artificial sequence
<220> FEATURE:
<223> OTHER INFORMATION: binding partner
<220> FEATURE:
<221> NAME/KEY: MISC_FEATURE
<223> OTHER INFORMATION: Xaa is any amino acid
<220> FEATURE:
<221> NAME/KEY: MISC_FEATURE
<222> LOCATION: (3)..(4)
<223> OTHER INFORMATION: Xaa is any amino acid

<400> SEQUENCE: 1

Cys Cys Xaa Xaa Cys Cys
1               5

<210> SEQ ID NO 2
<211> LENGTH: 8
<212> TYPE: PRT
<213> ORGANISM: artificial sequence
<220> FEATURE:
<223> OTHER INFORMATION: FLAG

<400> SEQUENCE: 2

Asp Tyr Lys Asp Asp Asp Asp Lys
1               5

<210> SEQ ID NO 3
<211> LENGTH: 9
<212> TYPE: PRT
<213> ORGANISM: artificial sequence
<220> FEATURE:
<223> OTHER INFORMATION: HA: influenza hemagglutinin epitope

<400> SEQUENCE: 3

Tyr Pro Tyr Asp Val Pro Phe Tyr Ala
1               5

<210> SEQ ID NO 4
<211> LENGTH: 4661
<212> TYPE: DNA
<213> ORGANISM: artificial sequence
<220> FEATURE:
<223> OTHER INFORMATION: prK5 vector
<220> FEATURE:
<221> NAME/KEY: promoter
<222> LOCATION: (15)..(591)
<223> OTHER INFORMATION: CMV early promoter
<220> FEATURE:
<221> NAME/KEY: enhancer
<222> LOCATION: (94)..(381)
```

```
<223> OTHER INFORMATION: CAG enhancer
<220> FEATURE:
<221> NAME/KEY: primer_bind
<222> LOCATION: (548)..(568)
<223> OTHER INFORMATION: CMV_fwd_primer_bind
<220> FEATURE:
<221> NAME/KEY: promoter
<222> LOCATION: (549)..(618)
<223> OTHER INFORMATION: CMV_promoter
<220> FEATURE:
<221> NAME/KEY: promoter
<222> LOCATION: (561)..(680)
<223> OTHER INFORMATION: CMV2_promoter
<220> FEATURE:
<221> NAME/KEY: primer_bind
<222> LOCATION: (592)..(611)
<223> OTHER INFORMATION: pCEP_fwd_primer_bind
<220> FEATURE:
<221> NAME/KEY: primer_bind
<222> LOCATION: (594)..(618)
<223> OTHER INFORMATION: LNCX_primer_bind
<220> FEATURE:
<221> NAME/KEY: primer_bind
<222> LOCATION: (828)..(845)
<223> OTHER INFORMATION: Sp6_primer_bind
<220> FEATURE:
<221> NAME/KEY: terminator
<222> LOCATION: (965)..(1108)
<223> OTHER INFORMATION: SV40_PA
<220> FEATURE:
<221> NAME/KEY: primer_bind
<222> LOCATION: (1065)..(1084)
<223> OTHER INFORMATION: EBV_rev_primer_bind
<220> FEATURE:
<221> NAME/KEY: primer_bind
<222> LOCATION: (1200)..(1220)
<223> OTHER INFORMATION: pBABE_3_primer_bind
<220> FEATURE:
<221> NAME/KEY: enhancer
<222> LOCATION: (1206)..(1421)
<223> OTHER INFORMATION: SV40_enhancer
<220> FEATURE:
<221> NAME/KEY: promoter
<222> LOCATION: (1218)..(1468)
<223> OTHER INFORMATION: SV40_promoter
<220> FEATURE:
<221> NAME/KEY: rep_origin
<222> LOCATION: (1385)..(1462)
<223> OTHER INFORMATION: SV40_rep_origin
<220> FEATURE:
<221> NAME/KEY: primer_bind
<222> LOCATION: (1447)..(1466)
<223> OTHER INFORMATION: SV40pro_F_primer_bind
<220> FEATURE:
<221> NAME/KEY: primer_bind
<222> LOCATION: (1554)..(1570)
<223> OTHER INFORMATION: M13_fwd20_primer_bind
<220> FEATURE:
<221> NAME/KEY: gene
<222> LOCATION: (1563)..(1706)
<223> OTHER INFORMATION: lacZ_a
<220> FEATURE:
<221> NAME/KEY: primer_bind
<222> LOCATION: (1563)..(1585)
<223> OTHER INFORMATION: M13_pUC_fwd_primer_bind
<220> FEATURE:
<221> NAME/KEY: rep_origin
<222> LOCATION: (1800)..(2106)
<223> OTHER INFORMATION: f1_rep_origin
<220> FEATURE:
<221> NAME/KEY: primer_bind
<222> LOCATION: (2374)..(2396)
<223> OTHER INFORMATION: pGEX_3_primer_bind
<220> FEATURE:
<221> NAME/KEY: promoter
<222> LOCATION: (2555)..(2583)
<223> OTHER INFORMATION: AmpR_promoter
<220> FEATURE:
<221> NAME/KEY: gene
<222> LOCATION: (2625)..(3485)
```

```
<223> OTHER INFORMATION: Ampicillin
<220> FEATURE:
<221> NAME/KEY: gene
<222> LOCATION: (2625)..(3485)
<223> OTHER INFORMATION: Orf frame 3
<220> FEATURE:
<221> NAME/KEY: rep_origin
<222> LOCATION: (3640)..(4259)
<223> OTHER INFORMATION: pBR322_rep_origin
<220> FEATURE:
<221> NAME/KEY: promoter
<222> LOCATION: (4568)..(4597)
<223> OTHER INFORMATION: lac_promoter
<220> FEATURE:
<221> NAME/KEY: primer_bind
<222> LOCATION: (4611)..(4633)
<223> OTHER INFORMATION: M13_pUC_rev_primer_bind

<400> SEQUENCE: 4
```

| | | | | | |
|---|---|---|---|---|---|
| ttcgagctcg | cccgacattg | attattgact | agttattaat | agtaatcaat | tacggggtca | 60 |
| ttagttcata | gcccatatat | ggagttccgc | gttacataac | ttacggtaaa | tggcccgcct | 120 |
| ggctgaccgc | ccaacgaccc | cgcccattg | acgtcaataa | tgacgtatgt | tcccatagta | 180 |
| acgccaatag | ggactttcca | ttgacgtcaa | tgggtggagt | atttacggta | aactgcccac | 240 |
| ttggcagtac | atcaagtgta | tcatatgcca | agtacgcccc | ctattgacgt | caatgacggt | 300 |
| aaatggcccg | cctggcatta | tgcccagtac | atgaccttat | gggactttcc | tacttggcag | 360 |
| tacatctacg | tattagtcat | cgctattacc | atggtgatgc | ggttttggca | gtacatcaat | 420 |
| gggcgtggat | agcggtttga | ctcacgggga | tttccaagtc | tccacccat | tgacgtcaat | 480 |
| gggagtttgt | tttggcacca | aaatcaacgg | gactttccaa | aatgtcgtaa | caactccgcc | 540 |
| ccattgacgc | aaatgggcgg | taggcgtgta | cggtgggagg | tctatataag | cagagctcgt | 600 |
| ttagtgaacc | gtcagatcgc | ctggagacgc | catccacgct | gttttgacct | ccatagaaga | 660 |
| caccgggacc | gatccagcct | ccgcggccgg | gaacggtgca | ttggaacgcg | gattccccgt | 720 |
| gccaagagtg | acgtaagtac | cgcctataga | gtctataggc | ccacccctt | ggcttcgtta | 780 |
| gaacgcggct | acaattaata | cataaccta | tgtatcatac | acatacgatt | taggtgacac | 840 |
| tatagaataa | catccacttt | gcctttctct | ccacaggtgt | ccactcccag | gtccaactgc | 900 |
| acctcggttc | tatcgattga | attccccggg | gatcctctag | agtcgacctg | cagaagcttg | 960 |
| gccgccatgg | cccaacttgt | ttattgcagc | ttataatggt | tacaaataaa | gcaatagcat | 1020 |
| cacaaatttc | acaaataaag | cattttttc | actgcattct | agttgtggtt | tgtccaaact | 1080 |
| catcaatgta | tcttatcatg | tctggatcgg | gaattaattc | ggcgcagcac | catggcctga | 1140 |
| aataacctct | gaaagaggaa | cttggttagg | taccttctga | ggcggaaaga | accagctgtg | 1200 |
| gaatgtgtgt | cagttagggt | gtggaaagtc | cccaggctcc | ccagcaggca | gaagtatgca | 1260 |
| aagcatgcat | ctcaattagt | cagcaaccag | gtgtggaaag | tccccaggct | ccccagcagg | 1320 |
| cagaagtatg | caaagcatgc | atctcaatta | gtcagcaacc | atagtcccgc | ccctaactcc | 1380 |
| gcccatcccg | cccctaactc | cgcccagttc | cgcccattct | ccgccccatg | gctgactaat | 1440 |
| tttttttatt | tatgcagagg | ccgaggccgc | ctcggcctct | gagctattcc | agaagtagtg | 1500 |
| aggaggcttt | tttggaggcc | taggcttttg | caaaaagctg | ttaacagctt | ggcactggcc | 1560 |
| gtcgttttac | aacgtcgtga | ctgggaaaac | cctggcgtta | cccaacttaa | tcgccttgca | 1620 |
| gcacatcccc | ctttcgccag | ctggcgtaat | agcgaagagg | cccgcaccga | tcgcccttcc | 1680 |
| caacagttgc | gcagcctgaa | tggcgaatgg | cgcctgatgc | ggtattttct | ccttacgcat | 1740 |
| ctgtgcggta | tttcacaccg | catacgtcaa | agcaaccata | gtacgcgccc | tgtagcggcg | 1800 |

```
cattaagcgc ggcgggtgtg gtggttacgc gcagcgtgac cgctacactt gccagcgccc      1860
tagcgcccgc tcctttcgct ttcttccctt cctttctcgc cacgttcgcc ggctttcccc      1920
gtcaagctct aaatcggggg ctcccttag ggttccgatt tagtgcttta cggcacctcg       1980
accccaaaaa acttgatttg ggtgatggtt cacgtagtgg gccatcgccc tgatagacgg      2040
tttttcgccc tttgacgttg gagtccacgt tctttaatag tggactcttg ttccaaactg      2100
gaacaacact caaccctatc tcgggctatt cttttgattt ataagggatt ttgccgattt      2160
cggcctattg gttaaaaaat gagctgattt aacaaaaatt taacgcgaat tttaacaaaa      2220
tattaacgtt tacaatttta tggtgcactc tcagtacaat ctgctctgat gccgcatagt      2280
taagccagcc ccgacacccg ccaacacccg ctgacgcgcc ctgacgggct tgtctgctcc      2340
cggcatccgc ttacagacaa gctgtgaccg tctccgggag ctgcatgtgt cagaggtttt      2400
caccgtcatc accgaaacgc gcgagacgaa agggcctcgt gatacgccta ttttatagg      2460 ttaatgtcat gataataatg gtttcttaga cgtcaggtgg cacttttcgg ggaaatgtgc      2520
gcggaacccc tatttgttta ttttctaaa tacattcaaa tatgtatccg ctcatgagac       2580
aataaccctg ataaatgctt caataatatt gaaaaaggaa gagtatgagt attcaacatt      2640
tccgtgtcgc ccttattccc ttttttgcgg cattttgcct tcctgttttt gctcacccag      2700
aaacgctggt gaaagtaaaa gatgctgaag atcagttggg tgcacgagtg ggttacatcg      2760
aactggatct caacagcggt aagatccttg agagttttcg ccccgaagaa cgttttccaa      2820
tgatgagcac ttttaaagtt ctgctatgtg gcgcggtatt atcccgtatt gacgccgggc      2880
aagagcaact cggtcgccgc atacactatt ctcagaatga cttggttgag tactcaccag      2940
tcacagaaaa gcatcttacg gatggcatga cagtaagaga attatgcagt gctgccataa      3000
ccatgagtga taacactgcg gccaacttac ttctgacaac gatcggagga ccgaaggagc      3060
taaccgcttt tttgcacaac atgggggatc atgtaactcg ccttgatcgt tgggaaccgg      3120
agctgaatga agccatacca aacgacgagc gtgacaccac gatgcctgta gcaatggcaa      3180
caacgttgcg caaactatta actggcgaac tacttactct agcttcccgg caacaattaa      3240
tagactggat ggaggcggat aaagttgcag gaccacttct gcgctcggcc cttccggctg      3300
gctggtttat tgctgataaa tctggagccg gtgagcgtgg gtctcgcggt atcattgcag      3360
cactggggcc agatggtaag ccctcccgta tcgtagttat ctacacgacg gggagtcagg      3420
caactatgga tgaacgaaat agacagatcg ctgagatagg tgcctcactg attaagcatt      3480
ggtaactgtc agaccaagtt tactcatata ctttagat tgatttaaaa cttcatttt        3540 aatttaaaag gatctaggtg aagatccttt ttgataatct catgaccaaa atcccttaac      3600
gtgagttttc gttccactga gcgtcagacc ccgtagaaaa gatcaaagga tcttcttgag      3660 atccttttt tctgcgcgta atctgctgct tgcaaacaaa aaaaccaccg ctaccagcgg       3720
tggtttgttt gccggatcaa gagctaccaa ctctttttcc gaaggtaact ggcttcagca      3780
gagcgcagat accaaatact gttcttctag tgtagccgta gttaggccac cacttcaaga      3840
actctgtagc accgcctaca tacctcgctc tgctaatcct gttaccagtg gctgctgcca      3900
gtggcgataa gtcgtgtctt accgggttgg actcaagacg atagttaccg gataaggcgc      3960
agcggtcggg ctgaacgggg ggttcgtgca cacagcccag cttggagcga acgacctaca      4020
ccgaactgag atacctacag cgtgagctat gagaaagcgc cacgcttccc gaagggagaa      4080
aggcggacag gtatccggta agcggcaggg tcggaacagg agagcgcacg agggagcttc      4140 caggggggaaa cgcctggtat ctttatagtc ctgtcgggtt tcgccacctc tgacttgagc     4200
```

-continued

```
gtcgattttt gtgatgctcg tcagggggc ggagcctatg gaaaaacgcc agcaacgcgg      4260 ccttttacg gttcctggcc ttttgctggc cttttgctca catgttcttt cctgcgttat      4320
cccctgattc tgtggataac cgtattaccg cctttgagtg agctgatacc gctcgccgca      4380
gccgaacgac cgagcgcagc gagtcagtga gcgaggaagc ggaagagcgc ccaatacgca      4440
aaccgcctct ccccgcgcgt tggccgattc attaatgcag ctggcacgac aggtttcccg      4500
actggaaagc gggcagtgag cgcaacgcaa ttaatgtgag ttagctcact cattaggcac      4560
cccaggcttt acactttatg cttccggctc gtatgttgtg tggaattgtg agcggataac      4620
aatttcacac aggaaacagc tatgacatga ttacgaatta a                         4661
```

<210> SEQ ID NO 5
<211> LENGTH: 8205
<212> TYPE: DNA
<213> ORGANISM: artificial sequence
<220> FEATURE:
<223> OTHER INFORMATION: HA-Snaptag-mGluR2 plasmid
<220> FEATURE:
<221> NAME/KEY: sig_peptide
<222> LOCATION: (937)..(1002)
<223> OTHER INFORMATION: mGluR5_sig_peptide
<220> FEATURE:
<221> NAME/KEY: misc_feature
<222> LOCATION: (1009)..(1035)
<223> OTHER INFORMATION: HA_CDS
<220> FEATURE:
<221> NAME/KEY: misc_feature
<222> LOCATION: (1042)..(1590)
<223> OTHER INFORMATION: Snaptag_CDS
<220> FEATURE:
<221> NAME/KEY: misc_feature
<222> LOCATION: (1597)..(4149)
<223> OTHER INFORMATION: mGluR2_CDS

<400> SEQUENCE: 5

```
aattcgagct cgcccgacat tgattattga ctagttatta atagtaatca attacggggt       60
cattagttca tagcccatat atggagttcc gcgttacata acttacggta aatggcccgc      120
ctggctgacc gcccaacgac ccccgcccat tgacgtcaat aatgacgtat gttcccatag      180
taacgccaat agggactttc cattgacgtc aatgggtgga gtatttacgg taaactgccc      240
acttggcagt acatcaagtg tatcatatgc caagtacgcc ccctattgac gtcaatgacg      300
gtaaatggcc cgcctggcat tatgcccagt acatgacctt atgggacttt cctacttggc      360
agtacatcta cgtattagtc atcgctatta ccatggtgat gcggttttgg cagtacatca      420
atgggcgtgg atagcggttt gactcacggg gatttccaag tctccacccc attgacgtca      480
atgggagttt gttttggcac caaaatcaac gggactttcc aaaatgtcgt aacaactccg      540
ccccattgac gcaaatgggc ggtaggcgtg tacggtggga ggtctatata agcagagctc      600
gtttagtgaa ccgtcagatc gcctggagac gccatccacg ctgttttgac ctccatagaa      660
gacaccggga ccgatccagc ctccgcggcc gggaacggtg cattggaagg cggattcccc      720
gtgccaagag tgacgtaagt accgcgtata gagtctatag gcccaccccc ttggcttcgt      780
tagaacgcgg ctacaattaa tacataacct tatgtatcat acacatacga tttaggtgac      840
actatagaat aacatccact ttgccttct ctccacaggt gtccactccc aggtccaact      900
gcacctcggt tctatcgatt gaattccttt cctaaaatgg tccttctgtt gatcctgtca      960
gtcctacttc tgaaagaaga gtgtacgagg agtgcacagt ccacgcgata cccctacgac     1020
gtacccgact acgccacgcg tggatccgac aaagactgcg aaatgaagcg caccacccctg     1080 gatagccctc tgggcaagct ggaactgtct ggtgcgaac agggcctgca cgagatcaag     1140
```

| | |
|---|---|
| ctgctgggca aaggaacatc tgccgccgac gccgtggaag tgcctgcccc agccgccgtg | 1200 |
| ctgggcggac cagagccact gatgcaggcc accgcctggc tcaacgccta ctttcaccag | 1260 |
| cctgaggcca tcgaggagtt ccctgtgcca gccctgcacc acccagtgtt ccagcaggag | 1320 |
| agctttaccc gccaggtgct gtggaaactg ctgaaagtgg tgaagttcgg agaggtcatc | 1380 |
| agctaccagc agctggccgc cctggccggc aatcccgccg ccaccgccgc cgtgaaaacc | 1440 |
| gccctgagcg gaaatcccgt gcccattctg atccccctgcc accgggtggt gtctagctct | 1500 |
| ggcgccgtgg ggggctacga gggcgggctc gccgtgaaag agtggctgct ggcccacgag | 1560 |
| ggccacagac tgggcaagcc tgggctgggc acgcgtaaga aggtgctgac cctggagggg | 1620 |
| gacctggtgc tgggtgggct gttcccagtg caccagaagg gtggcccagc cgaggagtgt | 1680 |
| ggacctgtta atgagcaccg aggcatacag cgcctagagg ctatgctttt tgcactggac | 1740 |
| cgcatcaacc gcgaccccca cctgctgcct ggtgtgcgct gggtgcgca catcctcgac | 1800 |
| agctgctcca aggatacaca cgccctggag caggcgctgg actttgtgcg tgcctcactc | 1860 |
| agtcgtggcg ctgacggctc acgccacatc tgtcctgatg gctcctatgc cacccacagt | 1920 |
| gatgctccta cagctgtcac cggtgtcatt ggtggctcct acagtgatgt ctccatccag | 1980 |
| gtggccaatc tcctgcggct gttccagatc ccacagatca gctatgcctc caccagtgcc | 2040 |
| aagctgagtg acaagtcccg ttacgattac tttgctcgca ctgtgccccc agacttcttc | 2100 |
| caagccaagg ccatggctga gattctccgc ttttttcaact ggacatatgt gtctacggtg | 2160 |
| gcatctgagg gtgactatgg tgagacaggc attgaggctt tcgagctcga ggctcgggca | 2220 |
| cgcaacatct gcgtggccac ttctgagaag gtgggccgtg ccatgagccg cgctgccttc | 2280 |
| gagggcgtgg tgcagccct gttgcagaaa cccagtgccc gtgtggctgt gctcttcacc | 2340 |
| cggtccgagg atgcccgtga gctgcttgca gccacccagc gcctcaacgc cagcttcaca | 2400 |
| tgggtggcca cgacggctg gggggccctg gagagcgtgg tggcaggcag tgaaagggct | 2460 |
| gctgagggcg ccatcaccat gaactggcc tcctacccca tcagtgactt tgcttcctac | 2520 |
| ttccagagct tggatccctg gaacaacagc agaaaccctt ggttccgtga gttctgggag | 2580 |
| gagaggttcc attgcagctt ccggcagcga gactgtgccg cccactctct gcgggccgtg | 2640 |
| ccctttgaac aggagtcaaa gatcatgttt gtggttaatg ccgtctatgc catggcccac | 2700 |
| gctctacaca acatgcaccg tgccctctgt cccaacacca cccacctctg cgatgctatg | 2760 |
| aggcctgtca atgggcgccg cctctacaaa gacttcgtgc tcaatgtcaa gtttgacgcc | 2820 |
| ccctttcgcc cagcagatac tgacgatgag gtccgcttcg accgctttgg tgacggtatt | 2880 |
| ggccgctaca acatcttcac ctatctgcgg gcaggcagtg ggcgctatcg ctaccagaag | 2940 |
| gtaggctact gggcagaagg tctgactctg gacactagct tcattccatg gcctccccca | 3000 |
| tcagccggac ctcttcctgc ctctcgctgt agcgagccct gccttcagaa cgaggtgaag | 3060 |
| agcgtgcagc cgggcgaggt ctgctgttgg ctctgcattc cctgtcagcc ctatgagtac | 3120 |
| aggctggatg agttcaccctg cgctgactgt ggcctgggct actggcctaa tgccagtctg | 3180 |
| actggctgct tgagctgcc ccaggagtac atccgctggg gtgatgcctg gcggtggga | 3240 |
| cctgtcacca tcgcctgcct gggtgccctg gcgacactct ttgtgttggg tgtctttgtg | 3300 |
| aggcataatg ccacacccgt ggtcaaggct tccggtcggg agctttgcta cattctgctg | 3360 |
| ggcggtgtct tcctttgcta ttgtatgacc ttcgtcttca ttgctaagcc ttccacggcc | 3420 |
| gtctgtacct tgaggcgcct cggtttgggt accgccttct ctgtctgcta ctcagccctc | 3480 |
| ctcaccaaga ccaatcgcat tgctcgcata tttggcgggg cccgggaggg tgcccagcgg | 3540 |

```
ccacgcttca tcagtcccgc ctcacaggtg gccatctgct tggcacttat ctcgggccag   3600
ctgctcattg tcgctgcctg gctggtggtg gaggcacctg gcacaggcaa ggagacagcc   3660
cctgaacggc gggaagtggt gacattgcgc tgtaaccacc gtgacgcgag catgctcggc   3720
tctctggcct acaatgtgct cctcatcgcg ctctgcacgc tctatgcctt caagacccgc   3780
aagtgcccgg agaacttcaa cgaagccaag ttcatcggct tcaccatgta caccacctgc   3840
atcatctggc tggcttttcct tcctatcttc tatgtcacct ccagtgatta tcgggtgcag   3900
accaccacga tgtgcgtgtc cgtcagcctc agtggctctg tggtgcttgg ctgcctcttt   3960
gcacccaagt tgcacatcat ccttttccag ccacagaaga atgtggtgag ccaccgggca   4020
cctaccagcc gctttggcag cgctgccccc agggccagcg ccaaccttgg tcaagggtct   4080
ggatcccagt ttgttcccac tgtttgcaac ggccgtgagg tggtggactc aacaacgtcg   4140
tcgctttgaa gatcccacac tcctgccctg acatggctgc tcccaaaccc agcatagacc   4200
ctcatccacg accaggagga agttggctgg gagcactgca ataacaccca ccccatgcct   4260
gcccccagag ccacttaccc acctcctgga ttcccagccc tttaggtcag aagccagagt   4320
ccttagctgg ggagcctctg caatggccag taactgtcct tgtagctatg ccccgtgttt   4380
gccaggcctg ggactcagag ggggagatga ccagtgtcta ctgtgttcta gagtcgacct   4440
gcagaagctt ggccgccatg gcccaacttg tttattgcag cttataatgg ttacaaataa   4500
agcaatagca tcacaaattt cacaaataaa gcattttttt cactgcattc tagttgtggt   4560
ttgtccaaac tcatcaatgt atcttatcat gtctggatcg atcgggaatt aattcggcgc   4620
agcaccatgg cctgaaataa cctctgaaag aggaacttgg ttaggtacct tctgaggcgg   4680
aaagaaccag ctgtggaatg tgtgtcagtt agggtgtgga aagtccccag gctccccagc   4740
aggcagaagt atgcaaagca tgcatctcaa ttagtcagca accaggtgtg gaaagtcccc   4800
aggctcccca gcaggcagaa gtatgcaaag catgcatctc aattagtcag caaccatagt   4860
cccgccccta actccgccca tcccgcccct aactccgccc agttccgccc attctccgcc   4920
ccatggctga ctaattttttt ttatttatgc agaggccgag gccgcctcgg cctctgagct   4980
attccagaag tagtgaggag gctttttggg aggcctaggc ttttgcaaaa agctgttaac   5040
agcttggcac tggccgtcgt tttacaacgt ggtgactggg aaaaccctgg cgttacccaa   5100
cttaatcgcc ttgcagcaca tccccccttc gccagctggc gtaatagcga agaggcccgc   5160
accgatcgcc cttcccaaca gttgcgtagc ctgaatggcg aatggcgcct gatgcggtat   5220
tttctcctta cgcatctgtg cggtatttca caccgcatac gtcaaagcaa ccatagtacg   5280
cgccctgtag cggcgcatta agcgcggcgg gtgtggtggt tacgcgcagc gtgaccgcta   5340
cacttgccag cgccctagcg cccgctcctt tcgctttctt cccttccttt ctcgccacgt   5400
tcgccggctt tccccgtcaa gctctaaatc ggggggctccc tttagggttg cgatttagtg   5460
ctttacggca cctcgacccc aaaaaacttg atttgggtga tggttcacgt agtgggccat   5520
cgccctgata dacggttttt cgcccttt ga cgttggagtc cacgttcttt aatagtggac   5580
tcttgttcca aactgaaca acactcaacc ctatctcggg ctattctttt gatttataag   5640
ggattttgcc gatttcggcc tattggttaa aaaatgagct gatttaacaa aaatttaacg   5700
cgaattttaa caaaatatta acgtttacaa ttttatggtg cactctcagt acaatctgct   5760
ctgatgccgc atagttaagc caactccgct atcgctacgt gactgggtca tggctgcgcc   5820
ccgacacccg ccaacacccg ctgacgcgcc ctgacgggct tgtctgctcc cggcatccgc   5880
ttacagacaa gctgtgaccg tctccgggag ctgcatgtgt cagaggtttt caccgtcatc   5940
```

```
accgaaacgc gcgaggcagt attcttgaag acgaaagggc ctcgtgatac gcctattttt    6000
ataggttaat gtcatgataa taatggtttc ttagacgtca ggtggcactt ttcggggaaa    6060
tgtgcgcgga accccttattt gtttattttt ctaaatacat tcaaatatgt atccgctcat   6120
gagacaataa ccctgataaa tgcttcaata atattgaaaa aggaagagta tgagtattca    6180
acatttccgt gtcgccctta ttccctttttt tgcggcattt tgccttcctg tttttgctca   6240
cccagaaacg ctggtgaaag taaaagatgc tgaagatcag ttgggtgcac gagtgggtta   6300
catcgaactg gatctcaaca gcggtaagat ccttgagagt tttcgccccg aagaacgttt   6360
tccaatgatg agcacttttta aagttctgct atgtggcgcg gtattatccc gtgatgacgc   6420
cgggcaagag caactcggtc gccgcataca ctattctcag aatgacttgg ttgagtactc   6480
accagtcaca gaaaagcatc ttacggatgg catgacagta agagaattat gcagtgctgc   6540
cataaccatg agtgataaca ctgcggccaa cttacttctg acaacgatcg gaggaccgaa   6600
ggagctaacc gcttttttgc acaacatggg ggatcatgta actcgccttg atcgttggga   6660
accggagctg aatgaagcca taccaaacga cgagcgtgac accacgatgc cagcagcaat   6720
ggcaacaacg ttgcgcaaac tattaactgg cgaactactt actctagctt cccggcaaca   6780
attaatagac tggatggagg cggataaagt tgcaggacca cttctgcgct cggcccttcc   6840
ggctggctgg tttattgctg ataaatctgg agccggtgag cgtgggtctc gcggtatcat   6900
tgcagcactg gggccagatg gtaagccctc ccgtatcgta gttatctaca cgacggggag   6960
tcaggcaact atggatgaac gaaatagaca gatcgctgag ataggtgcct cactgattaa   7020
gcattggtaa ctgtcagacc aagtttactc atatatactt tagattgatt taaaacttca   7080
ttttaatttt aaaaggatct aggtgaagat cctttttgat aatctcatga ccaaaatccc   7140
ttaacgtgag ttttcgttcc actgagcgtc agaccccgta gaaaagatca aggatcttc    7200
ttgagatcct ttttttctgc gcgtaatctg ctgcttgcaa acaaaaaaac caccgctacc   7260
agcggtggtt tgtttgccgg atcaagagct accaactctt tttccgaagg taactggctt   7320
cagcagagcg cagataccaa atactgtcct tctagtgtag ccgtagttag gccaccactt   7380
caagaactct gtagcaccgc ctacatacct cgctctgcta atcctgttac cagtggctgc   7440
tgccagtggc gataagtcgt gtcttaccgg gttggactca agacgatagt taccggataa   7500
ggcgcagcgg tcgggctgaa cggggggttc gtgcacacag cccagcttgg agcgaacgac   7560
ctacaccgaa ctgagatacc tacagcgtga gcattgagaa agcgccacgc ttcccgaagg   7620
gagaaaggcg gacaggtatc cggtaagcgg cagggtcgga acaggagagc gcacgaggga   7680
gcttccaggg ggaaacgcct ggtatcttta tagtcctgtc gggtttcgcc acctctgact   7740
tgagcgtcga tttttgtgat gctcgtcagg ggggcggagc ctatggaaaa acgccagcaa   7800
cgcggccttt ttacggttcc tggccttttg ctggcctttt gctcacatgt tctttcctgc   7860
gttatcccct gattctgtgg ataaccgtat taccgccttt gagtgagctg ataccgctcg   7920
ccgcagccga acgaccgagc gcagcgagtc agtgagcgag gaagcggaag agcgcccaat   7980
acgcaaaccg cctctccccg cgcgttggcc gattcattaa tccagctggc acgacaggtt   8040
tcccgactgg aaagcgggca gtgagcgcaa cgcaattaat gtgagttacc tcactcatta   8100
ggcaccccag gctttacact ttatgcttcc ggctcgtatg ttgtgtggaa ttgtgagcgg   8160
ataacaattt cacacaggaa acagctatga ccatgattac gaatt                   8205

<210> SEQ ID NO 6
<211> LENGTH: 8208
<212> TYPE: DNA
```

```
<213> ORGANISM: artificial sequence
<220> FEATURE:
<223> OTHER INFORMATION: Flag-Cliptag-mGluR2 plasmid
<220> FEATURE:
<221> NAME/KEY: sig_peptide
<222> LOCATION: (937)..(1002)
<223> OTHER INFORMATION: mGluR2_sig_peptide
<220> FEATURE:
<221> NAME/KEY: misc_feature
<222> LOCATION: (1015)..(1038)
<223> OTHER INFORMATION: FLAG_CDS
<220> FEATURE:
<221> NAME/KEY: misc_feature
<222> LOCATION: (1045)..(1593)
<223> OTHER INFORMATION: Cliptag_CDS

<400> SEQUENCE: 6
```

| | | | | | |
|---|---|---|---|---|---|
| aattcgagct | cgcccgacat | tgattattga | ctagttatta | atagtaatca | attaggggt | 60 |
| cattagttca | tagcccatat | atggagttcc | gcgttacata | acttacggta | aatggcccgc | 120 |
| ctggctgacc | gcccaacgac | ccccgcccat | tgacgtcaat | aatgacgtat | gttcccatag | 180 |
| taacgccaat | agggactttc | cattgacgtc | aatgggtgga | gtatttacgg | taaactgccc | 240 |
| acttggcagt | acatcaagtg | tatcatatgc | caagtacgcc | ccctattgac | gtcaatgacg | 300 |
| gtaaatggcc | cgcctggcat | tatgcccagt | acatgacctt | atgggacttt | cctacttggc | 360 |
| agtacatcta | cgtattagtc | atcgctatta | ccatggtgat | gcggttttgg | cagtacatca | 420 |
| atgggcgtgg | atagcggttt | gactcacggg | gatttccaag | tctccacccc | attgacgtca | 480 |
| atgggagttt | gttttggcac | caaaatcaac | gggactttcc | aaaatgtcgt | aacaactccg | 540 |
| ccccattgac | gcaaatgggc | ggtaggcgtg | tacggtggga | ggtctatata | agcagagctc | 600 |
| gtttagtgaa | ccgtcagatc | gcctggagac | gccatccacg | ctgttttgac | ctccatagaa | 660 |
| gacaccggga | ccgatccagc | ctccgcggcc | gggaacggtg | cattggaagg | cggattcccc | 720 |
| gtgccaagag | tgacgtaagt | accgcgtata | gagtctatag | gcccacccc | ttggcttcgt | 780 |
| tagaacgcgg | ctacaattaa | tacataacct | tatgtatcat | acacatacga | tttaggtgac | 840 |
| actatagaat | aacatccact | ttgccttct | ctccacaggt | gtccactccc | aggtccaact | 900 |
| gcacctcggt | tctatcgatt | gaattccttt | cctaaaatgg | tccttctgtt | gatcctgtca | 960 |
| gtcctacttc | tgaaagaaga | tgtacgaggg | agtgcacagt | ccacgcgacc | ggtagattat | 1020 |
| aaagatgacg | atgacaaaac | gcgaggatcc | gacaaggatt | gtgaaatgaa | acgcaccaca | 1080 |
| ctggacagcc | ctttggggaa | gctggagctg | tctggttgtg | agcagggtct | gcacgaaata | 1140 |
| attttctgg | gcaaggggac | gtctgcagct | gatgccgtgg | aggtcccagc | ccccgctgcg | 1200 |
| gttctcggag | gtccggagcc | cctgatacag | gctacagcct | ggctgaatgc | ctatttccac | 1260 |
| cagcccgagg | ctatcgaaga | gttccccgtg | ccggctcttc | accatcccgt | tttccagcaa | 1320 |
| gagtcgttca | ccagacaggt | gttatggaag | ctgctgaagg | ttgtgaaatt | cggagaagtg | 1380 |
| atttctgagt | cacacttagc | agccctggta | ggcaaccccg | cagccacggc | agcagtgaat | 1440 |
| acggcactgg | atggcaatcc | tgtccctatc | ctgatcccgt | gccacagagt | ggtccagggg | 1500 |
| gattcggatg | tggggccgta | ccttggtgga | ctggccgtga | aggaatggct | tctggcccat | 1560 |
| gaaggccacc | ggttggggaa | gccaggcttg | ggaacgcgta | agaaggtgct | gaccctggag | 1620 |
| ggggacctgg | tgctgggtgg | gctgttccca | gtgcaccaga | agggtggccc | agccgaggag | 1680 |
| tgtggacctg | ttaatgagca | ccgaggcata | cagcgcctag | aggctatgct | ttttgcactg | 1740 |
| gaccgcatca | accgcgaccc | ccacctgctg | cctggtgtgc | gcttgggtgc | gcacatcctc | 1800 |
| gacagctgct | ccaaggatac | acacgccctg | gagcaggcgc | tggactttgt | gcgtgcctca | 1860 |

```
ctcagtcgtg gcgctgacgg ctcacgccac atctgtcctg atggctccta tgccacccac   1920
agtgatgctc ctacagctgt caccggtgtc attggtggct cctacagtga tgtctccatc   1980
caggtggcca atctcctgcg gctgttccag atcccacaga tcagctatgc ctccaccagt   2040
gccaagctga gtgacaagtc ccgttacgat tactttgctc gcactgtgcc cccagacttc   2100
ttccaagcca aggccatggc tgagattctc cgcttttttca actggacata tgtgtctacg   2160
gtggcatctg agggtgacta tggtgagaca ggcattgagg ctttcgagct cgaggctcgg   2220
gcacgcaaca tctgcgtggc cacttctgag aaggtgggcc gtgccatgag ccgcgctgcc   2280
ttcgagggcg tggtgcgagc cctgttgcag aaacccagtg cccgtgtggc tgtgctcttc   2340
acccggtccg aggatgcccg tgagctgctt gcagccaccc agcgcctcaa cgccagcttc   2400
acatgggtgg ccagcgacgg ctggggggcc ctggagagcg tggtggcagg cagtgaaagg   2460
gctgctgagg gcgccatcac cattgaactg gcctcctacc ccatcagtga ctttgcttcc   2520
tacttccaga gcttggatcc ctggaacaac agcagaaacc cttggttccg tgagttctgg   2580
gaggagaggt tccattgcag cttccggcag cgagactgtg ccgcccactc tctgcgggcc   2640 gtgcccttg aacaggagtc aaagatcatg tttgtggtta atgccgtcta tgccatggcc   2700
cacgctctac acaacatgca ccgtgccctc tgtcccaaca ccacccacct ctgcgatgct   2760
atgaggcctg tcaatgggcg ccgcctctac aaagacttcg tgctcaatgt caagtttgac   2820
gccccctttc gcccagcaga tactgacgat gaggtccgct tcgaccgctt tggtgacggt   2880
attggccgct acaacatctt cacctatctg cgggcaggca gtgggcgcta tcgctaccag   2940
aaggtaggct actgggcaga aggtctgact ctggacacta gcttcattcc atgggcctcc   3000
ccatcagccg gacctcttcc tgcctctcgc tgtagcgagc cctgccttca gaacgaggtg   3060
aagagcgtgc agccgggcga ggtctgctgt tggctctgca ttccctgtca gccctatgag   3120
tacaggctgg atgagttcac ctgcgctgac tgtggcctgg gctactgcc taatgccagt   3180 ctgactggct gctttgagct gccccaggag tacatccgct ggggtgatgc ctgggcggtg   3240
ggacctgtca ccatcgcctg cctgggtgcc ctggcgacac tctttgtgtt gggtgtcttt   3300
gtgaggcata atgccacacc cgtggtcaag gcttccggtc gggagctttg ctacattctg   3360
ctgggcggtg tcttcctttg ctattgtatg accttcgtct tcattgctaa gccttccacg   3420
gccgtctgta ccttgaggcg cctcggtttg gtaccgcct tctctgtctg ctactcagcc   3480
ctcctcacca agaccaatcg cattgctcgc atatttggcg gggcccggga gggtgcccag   3540
cggccacgct tcatcagtcc cgcctcacag gtggccatct gcttggcact tatctcgggc   3600
cagctgctca ttgtcgctgc ctggctggtg gtggaggcac ctggcacagg caaggagaca   3660 gccccctgaac ggcggaagt ggtgacattg cgctgtaacc accgtgacgc gagcatgctc   3720
ggctctctgg cctacaatgt gctcctcatc gcgctctgca cgctctatgc cttcaagacc   3780
cgcaagtgcc cggagaactt caacgaagcc aagttcatcg gcttcaccat gtacaccacc   3840
tgcatcatct ggctggcttt ccttcctatc ttctatgtca cctccagtga ttatcgggtg   3900
cagaccacca cgatgtgcgt gtccgtcagc ctcagtggct ctgtggtgct ggctgcctc   3960 tttgcaccca agttgcacat catcctttc cagccacaga agaatgtggt gagccaccgg   4020
gcacctacca gccgctttgg cagcgctgcc cccaggccca cgccaacct tggtcaaggg   4080 tctggatccc agtttgttcc cactgtttgc aacggccgtg aggtggtgga ctcaacaacg   4140
tcgtcgcttt gaagatccca cactcctgcc ctgacatggc tgctcccaaa ccagcatag   4200 accctcatcc acgaccagga ggaagttggc tgggagcact gcaataacac ccaccccatg   4260
```

```
cctgccccca gagccactta cccacctcct ggattcccag ccctttaggt cagaagccag   4320
agtccttagc tggggagcct ctgcaatggc cagtaactgt ccttgtagct atgcccgtg    4380 tttgccaggc ctgggactca gagggggaga tgaccagtgt ctactgtgtt ctagagtcga   4440
cctgcagaag cttggccgcc atggcccaac ttgtttattg cagcttataa tggttacaaa   4500
taaagcaata gcatcacaaa tttcacaaat aaagcatttt tttcactgca ttctagttgt   4560
ggtttgtcca aactcatcaa tgtatcttat catgtctgga tcgatcggga attaattcgg   4620
cgcagcacca tggcctgaaa taacctctga agaggaact  tggttaggta ccttctgagg   4680
cggaaagaac cagctgtgga atgtgtgtca gttagggtgt ggaaagtccc caggctcccc   4740
agcaggcaga agtatgcaaa gcatgcatct caattagtca gcaaccaggt gtggaaagtc   4800
cccaggctcc ccagcaggca gaagtatgca aagcatgcat ctcaattagt cagcaaccat   4860
agtcccgccc ctaactccgc ccatcccgcc cctaactccg cccagttccg cccattctcc   4920
gccccatggc tgactaattt ttttatttta tgcagaggcc gaggccgcct cggcctctga   4980
gctattccag aagtagtgag gaggcttttt tggaggccta ggcttttgca aaaagctgtt   5040
aacagcttgg cactggccgt cgttttacaa cgtggtgact gggaaaaccc tggcgttacc   5100
caacttaatc gccttgcagc acatcccccc ttcgccagct ggcgtaatag cgaagaggcc   5160
cgcaccgatc gcccttccca acagttgcgt agcctgaatg gcgaatggcg cctgatgcgg   5220
tattttctcc ttacgcatct gtgcggtatt tcacaccgca tacgtcaaag caaccatagt   5280
acgcgccctg tagcggcgca ttaagcgcgg cgggtgtggt ggttacgcgc agcgtgaccg   5340
ctacacttgc cagcgcccta gcgcccgctc ctttcgcttt cttcccttcc tttctcgcca   5400
cgttcgccgg ctttccccgt caagctctaa atcgggggct ccctttaggg ttgcgattta   5460
gtgctttacg gcacctcgac cccaaaaaac ttgatttggg tgatggttca cgtagtgggc   5520
catcgccctg atagacggtt tttcgccctt gacgttgga  gtccacgttc tttaatagtg   5580
gactcttgtt ccaaactgga acaacactca acccctatctc gggctattct tttgatttat   5640
aagggatttt gccgatttcg gcctattggt taaaaaatga gctgatttaa caaaaattta   5700
acgcgaattt taacaaaata ttaacgttta caattttatg gtgcactctc agtacaatct   5760
gctctgatgc cgcatagtta agccaactcc gctatcgcta cgtgactggg tcatggctgc   5820
gccccgacac ccgccaacac ccgctgacgc gccctgacgg gcttgtctgc tcccggcatc   5880
cgcttacaga caagctgtga ccgtctccgg gagctgcatg tgtcagaggt tttcaccgtc   5940
atcaccgaaa cgcgcgaggc agtattcttg aagacgaaag gcctcgtga  tacgcctatt   6000 tttataggtt aatgtcatga taataatggt ttcttagacg tcaggtggca cttttcgggg   6060
aaatgtgcgc ggaaccccta tttgtttatt tttctaaata cattcaaata tgtatccgct   6120
catgagacaa taaccctgat aaatgcttca ataatattga aaaggaaga  gtatgagtat   6180 tcaacatttc cgtgtcgccc ttattccctt ttttgcggca ttttgccttc ctgttttgc    6240 tcacccagaa acgctggtga agtaaaaga  tgctgaagat cagttgggtg cacgagtggg   6300
ttacatcgaa ctggatctca acagcggtaa gatccttgag agttttcgcc ccgaagaacg   6360
ttttccaatg atgagcactt ttaaagttct gctatgtggc gcggtattat cccgtgatga   6420
cgccgggcaa gagcaactcg gtcgccgcat acactattct cagaatgact tggttgagta   6480
ctcaccagtc acagaaaagc atcttacgga tggcatgaca gtaagagaat tatgcagtgc   6540
tgccataacc atgagtgata acactgcggc caacttactt ctgacaacga tcggaggacc   6600
gaaggagcta accgcttttt tgcacaacat ggggatcat  gtaactcgcc ttgatcgttg   6660
```

```
ggaaccggag ctgaatgaag ccataccaaa cgacgagcgt gacaccacga tgccagcagc    6720
aatggcaaca acgttgcgca aactattaac tggcgaacta cttactctag cttcccggca    6780
acaattaata gactggatgg aggcggataa agttgcagga ccacttctgc gctcggccct    6840
tccggctggc tggtttattg ctgataaatc tggagccggt gagcgtgggt ctcgcggtat    6900
cattgcagca ctggggccag atggtaagcc ctcccgtatc gtagttatct acacgacggg    6960
gagtcaggca actatggatg aacgaaatag acagatcgct gagataggtg cctcactgat    7020
taagcattgg taactgtcag accaagttta ctcatatata ctttagattg atttaaaact    7080
tcatttttaa tttaaaagga tctaggtgaa gatccttttt gataatctca tgaccaaaat    7140
cccttaacgt gagttttcgt tccactgagc gtcagacccc gtagaaaaga tcaaaggatc    7200
ttcttgagat cctttttttc tgcgcgtaat ctgctgcttg caaacaaaaa aaccaccgct    7260
accagcggtg gtttgtttgc cggatcaaga gctaccaact cttttccga aggtaactgg    7320 cttcagcaga gcgcagatac caaatactgt ccttctagtg tagccgtagt taggccacca    7380
cttcaagaac tctgtagcac cgcctacata cctcgctctg ctaatcctgt taccagtggc    7440
tgctgccagt ggcgataagt cgtgtcttac cgggttggac tcaagacgat agttaccgga    7500
taaggcgcag cggtcgggct gaacggggggt tcgtgcaca cagcccagct tggagcgaac    7560
gacctacacc gaactgagat acctacagcg tgagcattga aaagcgcca cgcttcccga    7620 agggagaaag gcggacaggt atccggtaag cggcagggtc ggaacaggag agcgcacgag    7680
ggagcttcca gggggaaacg cctggtatct ttatagtcct gtcgggtttc gccacctctg    7740
acttgagcgt cgatttttgt gatgctcgtc aggggggcgg agcctatgga aaaacgccag    7800
caacgcggcc ttttacggtt cctggccctt ttgctggcct tttgctcaca tgttctttcc    7860
tgcgttatcc cctgattctg tggataaccg tattaccgcc tttgagtgag ctgataccgc    7920
tcgccgcagc cgaacgaccg agcgcagcga gtcagtgagc gaggaagcgg aagagcgccc    7980
aatacgcaaa ccgcctctcc ccgcgcgttg gccgattcat taatccagct ggcacgacag    8040
gtttcccgac tggaaagcgg gcagtgagcg caacgcaatt aatgtgagtt acctcactca    8100
ttaggcaccc caggctttac actttatgct tccggctcgt atgttgtgtg gaattgtgag    8160
cggataacaa tttcacacag gaaacagcta tgaccatgat tacgaatt              8208
```

```
<210> SEQ ID NO 7
<211> LENGTH: 26
<212> TYPE: PRT
<213> ORGANISM: artificial sequence
<220> FEATURE:
<223> OTHER INFORMATION: GPI anchor

<400> SEQUENCE: 7

Arg Arg Ser Ser Ser Thr Val Leu Phe Ser Ser Pro Val Ile Leu Leu
1               5                   10                  15

Ile Ser Phe Leu Ile Phe Leu Ile Val Gly
            20                  25

<210> SEQ ID NO 8
<211> LENGTH: 5
<212> TYPE: PRT
<213> ORGANISM: artificial sequence
<220> FEATURE:
<223> OTHER INFORMATION: CRD

<400> SEQUENCE: 8

Leu Pro Gln Glu Tyr
1               5
```

```
<210> SEQ ID NO 9
<211> LENGTH: 6
<212> TYPE: PRT
<213> ORGANISM: artificial sequence
<220> FEATURE:
<223> OTHER INFORMATION: VFT domain

<400> SEQUENCE: 9

Gly Pro Leu Pro Ala Ser
1               5
```